(12) United States Patent
Gangjee et al.

(10) Patent No.: US 10,611,767 B2
(45) Date of Patent: Apr. 7, 2020

(54) SELECTIVE PROTON COUPLED FOLATE TRANSPORTER AND FOLATE RECEPTOR, AND GARFTASE INHIBITOR COMPOUNDS AND METHODS OF USING THE SAME

(71) Applicants: Duquesne University of the Holy Spirit, Pittsburgh, PA (US); WAYNE STATE UNIVERSITY, Detroit, MI (US)

(72) Inventors: Aleem Gangjee, Allison Park, PA (US); Larry H. Matherly, Novi, MI (US)

(73) Assignees: Duquesne University of the Holy Spirit, Pittsburgh, PA (US); Wayne State University, Detroit, MI (US)

( * ) Notice: Subject to any disclaimer, the term of this patent is extended or adjusted under 35 U.S.C. 154(b) by 0 days.

(21) Appl. No.: 16/000,954

(22) Filed: Jun. 6, 2018

(65) Prior Publication Data
US 2018/0346474 A1    Dec. 6, 2018

Related U.S. Application Data

(62) Division of application No. 15/342,359, filed on Nov. 3, 2016, now Pat. No. 10,000,498, which is a division of application No. 13/558,873, filed on Jul. 26, 2012, now Pat. No. 9,511,069, which is a division of application No. 12/242,988, filed on Oct. 1, 2008, now Pat. No. 8,252,804.

(51) Int. Cl.
| | |
|---|---|
| *C07D 493/04* | (2006.01) |
| *A61P 35/04* | (2006.01) |
| *A61K 31/519* | (2006.01) |
| *C07D 487/04* | (2006.01) |
| *C07D 495/04* | (2006.01) |

(52) U.S. Cl.
CPC .......... *C07D 487/04* (2013.01); *A61K 31/519* (2013.01); *A61P 35/04* (2018.01); *C07D 495/04* (2013.01)

(58) Field of Classification Search
CPC ............................ C07D 493/04; A61K 31/519
USPC ........................................ 544/278; 514/260.1
See application file for complete search history.

(56) References Cited

U.S. PATENT DOCUMENTS

| | | | |
|---|---|---|---|
| 5,028,608 A | 7/1991 | Taylor et al. | |
| 5,248,775 A | 9/1993 | Taylor et al. | |
| 5,317,019 A | 5/1994 | Bender et al. | |
| 5,354,754 A | 10/1994 | Akimoto et al. | |
| 6,518,426 B1 | 2/2003 | Gangjee | |
| 6,525,050 B1 | 2/2003 | Romines, III et al. | |
| 2004/0096436 A1 | 5/2004 | Carson et al. | |
| 2005/0032786 A1 | 2/2005 | Kajino et al. | |
| 2005/0153989 A1 | 7/2005 | Grotzfeld et al. | |
| 2006/0178380 A1 | 8/2006 | Gangjee | |
| 2008/0045552 A1 | 2/2008 | Gangjee et al. | |
| 2010/0081676 A1 | 4/2010 | Gangjee et al. | |
| 2012/0295926 A1 | 11/2012 | Gangjee et al. | |

FOREIGN PATENT DOCUMENTS

| | | |
|---|---|---|
| CN | 101195625 | 6/2008 |
| EP | 0148924 A2 | 3/1991 |
| EP | 0438261 A2 | 7/1991 |
| EP | 0549291 A1 | 6/1993 |
| JP | 3-173890 | 7/1991 |
| JP | 4-117381 | 4/1992 |
| JP | 5-78362 | 3/1993 |
| JP | 5-186437 | 7/1993 |
| JP | 6-172358 | 6/1994 |
| JP | 2000-516961 | 12/2000 |
| WO | 9603406 | 2/1996 |
| WO | 9808382 | 3/1998 |
| WO | 2008/027949 A2 | 3/2008 |

OTHER PUBLICATIONS

General Chemistry Dictionary from ACS website, http://chemistry.science-dictionary.org/General-Chemistry-Dictionary/homologue, downloaded Dec. 16, 2013, p. 1.

(Continued)

*Primary Examiner* — Susanna Moore
(74) *Attorney, Agent, or Firm* — Buchanan Ingersoll & Rooney PC; Craig G. Cochenour, Esq.

(57) ABSTRACT

Fused cyclic pyrimidine compounds, including tautomers thereof, and pharmaceutically acceptable salts, prodrugs, solvates and hydrates thereof, are disclosed having the general Formula I:

These compounds are useful in methods for treating cancer, selectively targeting cancerous cells via the proton coupled folate transporter, folate receptor alpha, and/or folate receptor beta pathways, inhibiting GARFTase in cancerous cells, and selectively targeting activated macrophages in a patient having an autoimmune disease, such as rheumatoid arthritis.

7 Claims, 6 Drawing Sheets

(56) References Cited

OTHER PUBLICATIONS

International Search Report and Written Opinion of the International Searching Authority for PCT/US11/55584 dated May 2, 2012.
International Search Report and the Written Opinion of the International Searching Authority for PCT/US2009/058968 dated Feb. 3, 2010 (Forms PCT/ISA/220, PCT/ISA/210, PCT/ISA/237).
International Preliminary Report on Patentability for PCT/US2009/058968 dated Sep. 7, 2011 (Form PCT/IPEA/409).
Vippagunta et al., "Crystalline Solids", Adv. Drug. Deily. Rev. May 16, 2001;48(1):3-26.
Banker et al., "Modem Pharmaceutics, 3ed.", Marcel Dekker, New York; 1996, p. 596.
Wolff, "Burger's Medicinal Chemistry, 5ed, Part I", John Wiley & Sons, 1995, pp. 975-977.
Xu, Yun et al., Synthesis of Pyrrolo[2,3-d]Pyrimidine Analogues: "Pyridine Ring" Analogues of Pemetrexed, Heterocycles, 2009, 2353-2360, vol. 79, No. 9, the Japan Institute of Heterocyclic Chemistry.
Kotake, Yoshihiko et al., Novel 6-5 Fused Ring Heterocycle Antifolates with Potent Antitumor Activity: Bridge Modifications and Heterocyclic Benzoyl Isosters of 2,4-Diamino-6,7-dihydo-5H-cyclopental[d]pyrimidine Antifolate, Chem. Pharm. Bull, May 1995, 829-841, 43(5), Pharmaceutical Society of Japan.
Parenti, Marco Daniele et al., Three Dimensional Quantitative Structure-Activity Relationship Analysis of a Set of Plasmodium falciparum Dihydrofolate Reductase Inhibitors Using a Pharmacophore Generation Approach, J. Med. Chem., 2004, vo. 47, 4258-4267, American Chemical Society.

| Code | IC$_{50}$ KB nM | PC43 | R2 | IC$_{50}$ RT16 (alpha) nM | RT16+F | % RFC transport | FRalpha relative affinity | FR alpha Binding % |
|---|---|---|---|---|---|---|---|---|
| AAG154353 | 0.25 | N | N | 2 | N | 66.47 | 1.03 | 33 |
| AAG154360 | 3.4 | N | N | 2 | N | | 0.72 | 43.1 |
| AAG154489 | 0.3 | | | | | | | |
| AAG154468 | 122 | | | | | | | |
| AAG154479 | N | | | | | | | |
| AAG154484 | N | | | | | | | |

N = no activity

Figure 2

Compound AAG120366-2 (n=3)

SELECTIVE PROTON COUPLED FOLATE TRANSPORTER AND FOLATE RECEPTOR, AND GARFTASE INHIBITOR COMPOUNDS AND METHODS OF USING THE SAME

CROSS-REFERENCE TO RELATED APPLICATIONS

This utility patent application is a divisional patent application of and claims the benefit of co-pending prior U.S. patent application Ser. No. 15/342,359, filed Nov. 3, 2016, which is a divisional patent application of Ser. No. 13/558,873, filed on Jul. 26, 2012, now U.S. Pat. No. 9,511,069, granted on Dec. 6, 2016, which is a divisional application of U.S. patent application Ser. No. 12/242,988, filed Oct. 1, 2008, now U.S. Pat. No. 8,252,804, granted on Aug. 28, 2012. The entire contents U.S. patent application Ser. Nos. 15/342,359, 13/558,873 and 12/242,988, are incorporated by reference into this divisional utility patent application.

STATEMENT REGARDING FEDERALLY SPONSORED RESEARCH OR DEVELOPMENT

This invention was made with government support under Contract No. R01 CA125153 awarded by the National Institutes of Health, U.S. Department of Health and Human Services. The government has certain rights in the invention.

BACKGROUND OF THE INVENTION

1. Field of the Invention

The present invention relates to selective proton coupled folate transporter (PCFT) and alpha folate receptor (FR alpha), beta folate receptor (FR beta), and glycinamide ribonucleotide formyltransferase (GARFTase) enzyme inhibitor compounds, and their methods of use. Preferably, these compounds have heterocycloalkyl-carbonyl-L-glutamate substituents or heterocycloaryl-carbonyl-L-glutamate substituents. The compounds of this invention may be made into salts that are water soluble for providing orally active selective antitumor agents.

2. Description of the Background Art

Known cancer chemotherapy agents target both normal and cancerous tumor cells. This lack of selectivity for tumor cells results in cytotoxicity to the normal cells and is one of the major causes of chemotherapeutic failure in the treatment of cancer. Further, advanced stage and chemotherapeutic agent resistant tumors may be difficult to treat with know chemotherapeutic agents such as for example but not limited to carboplatin or paclitaxel (docitaxel).

Folates are members of the B Class of vitamins that are cofactors for the synthesis of nucleotide precursors. serine and methionine in one-carbon transfer reactions. Since mammals cannot synthesize folates de novo, cellular uptake of these derivatives is essential for cell growth and tissue regeneration. Reflecting their hydrophilic anionic character, folates do not cross biological membranes by diffusion alone. Accordingly, mammalian cells have evolved sophisticated membrane transport systems for facilitating accumulation of folates.

The ubiquitously expressed reduced folate carrier (RFC) is the major transport system for folates in mammalian cells and mediates concentrative uptake of folate substrates. RFC is a member of the major facilitator superfamily of transporters and is an integral transmembrane protein with micromolar affinity for its physiologic substrate, 5-methyl tetrahydrofolate. Importantly, RFC is also the primary transporter of clinically relevant antifolate drugs used for cancer including methotrexate (MTX), raltitrexed (ZD1694, Tomudex) (RTX), and pemetrexed (LY231514, Alimta) (PMX). Loss of RFC levels or function is a common mode of antifolate resistance. While a previously unrecognized proton-coupled folate transporter (PCFT) was recently reported to contribute to folate absorption in the duodenum, its tissue-specificity and overall role in folate homeostasis are not clear yet.

The family of folate receptors (FRs) represents yet another mode of folate uptake into mammalian cells. The FRs are high affinity folate binding proteins encoded by three distinct genes, designated FR alpha, FR beta and FR gamma, localized to chromosome 11q13.3-q13.5. In contrast to RFC and PCFT, FR alpha and FR beta are anchored in plasma membranes by a glycosyl phosphatidylinositol (GPI) anchor. FR gamma contains no GPI anchor and is secreted. Whereas FR alpha and FR beta (but not FR gamma) mediate cellular accumulation of folate at low (nanomolar) concentrations by receptor-mediated endocytosis, these homologous proteins show differences in binding affinities for reduced folate substrates.

The high affinity FRs offer a potential means of selective tumor targeting, given their restricted pattern of tissue expression and function. For instance, FR alpha is expressed on the apical membrane surface of normal tissues such as kidney, placenta, and choroid plexus, whereas FR beta is expressed in placenta, spleen, and thymus. Importantly, FR alpha is overexpressed in a number of carcinomas including up to 90% of ovarian cancers. Close associations were reported between FR alpha expression levels with grade and differentiation status of ovarian tumors. FR alpha in normal tissues (unlike tumors) is reported to be inaccessible to the circulation. FR beta is expressed in a wide range of myeloid leukemia cells. FR beta in normal hematopoetic cells differs from that in leukemia cells in its inability to bind folate ligand.

Folate-conjugated cytotoxins, liposomes, or radionuclides, or cytoxic antifolates have all been used to target FRs. Unfortunately, for most folate-based therapeutics such as classical antifolates (including RTX, PMX, and lometrexol (LMX)), tumor selectivity is lost since substrates are shared between FRs and the ubiquitously expressed RFC. Indeed, this likely explains the severe myelosupression encountered in phase 1 studies with LMX.

If, a FR-targeted ligand were itself cytotoxic without RFC activity, selective tumor targeting would ensue. Antifolates that selectively target FRs over RFC have been described including CB3717 and, more recently, cyclopenta[g]quinazoline antifolates BGC638 and BGC945, all of which potently inhibit thymidylate synthase (TS) within cells. When BGC945 was tested in mice, there was no toxicity to normal tissues, as reflected in weight loss, nor were there any macroscopic signs of toxicity to major organs, consistent with the premise that FR targeting is highly selective.

As is known by those skilled in the art, FRs such as FR alpha and FR beta are overexpressed on a substantial amount of certain surfaces of a number of types of cancerous tumors. FR alpha is known to be overexpressed in ovarian, endometrial, kidney, lung, mesothelioma, breast and brain tumors. FR beta is known to be overexpressed in acute myeloid leukemias In most normal cells, the FRs are not present. In most normal cells, folic acid is not taken up by way of a reduced folate carrier (RFC) system. Uptake of folates and antifolates by tissues and tumors is primarily by the ubiquitously expressed RFC system. In light of the specificity of folic acid, conjugates of folic acid have been used to selectively deliver toxins, liposomes, imaging agents, and cytotoxic agents to FR expressing tumors. The major limitation of the folic acid conjugates is that they require cleavage from the folic acid moiety to release, for example, the cytotoxic agent. Cleavage of the cytotoxic agent moiety from the folic acid conjugate is often difficult to achieve and the anti-tumor activity is hindered or is nonexistent as a result of the inability or reduced ability to release the cytotoxic agent. Another limitation of the folic acid conjugates entails premature release of the cytotoxic agent during transport and before reaching the cancerous tumor. The premature release thus leads to undesired toxicity in normal cells.

The FRs alpha and beta represent another mode of folate uptake and are considered by those skilled in the art to be potential chemotherapeutic targets for selective tumor uptake. US Patent Application Publication No. US 2008/0045710 A1, published Feb. 21, 2008 (Aleem Gangjee) describes compounds for treating cancer tumors wherein fused cyclic pyrimidines are used to selectively target FRs of cancerous tumors that express FR alpha and FR beta and that inhibit glycinamide ribonucleotide formyltransferase (GARFTase) enzyme. The compounds are not significantly taken up by a cell or tissue using the RFC system.

There is a need for single compounds having potent anti-tumor activity that selectively target FR alpha and FR beta of cancerous cells, that inhibit GARFTase in cancerous cells, and that have a negligible substrate activity for RFC.

SUMMARY OF THE INVENTION

The present invention meets the above need by providing selective proton coupled folate transporter (PCFT) and alpha and beta FR, and GARTFase enzyme inhibitor compounds.

The present invention provides a compound comprising Formula I:

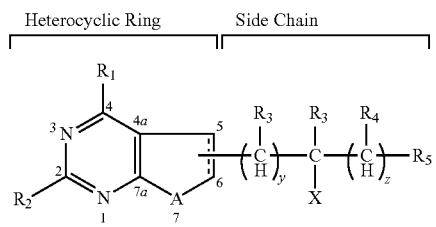

I wherein $R_1$ comprises one of (a) a hydrogen (H)), (b) an OH, (c) $CH_3$, and (d) NHR wherein R is either a H or an alkyl group having from 1 to 6 carbon atoms, and tautomers of (b) and (d); $R_2$ comprises one of (a) a hydrogen (H), (b) a $CH_3$, (c) an OH, and (d) NHR wherein R is either a H or an alkyl group having from 1 to 6 carbon atoms; A comprises one of (a) CR'R'', (b) NR', wherein R' and R'' are the same or different and are either a H or an alkyl group having from 1 to 6 carbon atoms, (c) a sulfur (S), and (d) an oxygen (O); wherein the bond at position 5-6 may either be a single or a double bond; wherein the five membered ring has a side chain attached at positions 5, 6 or 7, and wherein when said side chain attachment is at position 7 then A comprises one of (a) CR', and (b) N, and optionally includes wherein the carbon atoms at positions 5 and 6, independently, have attached thereto either (a) two hydrogen atoms if the bond between carbon atoms 5 and 6 is a single bond or one hydrogen atom if the bond between carbon atoms 5 and 6 is a double bond, or (b) an alkyl group having from one to six carbon atoms and a hydrogen atom if the bond between carbon atoms at positions 5 and 6 is a single bond or an alkyl group having from one to six carbon atoms if the bond between carbon atoms 5 and 6 is a double bond, and combinations thereof; and $R_3$ comprises one of (a) a hydrogen (H), (b) $CH_3$, (c) trifluoromethyl, (d) difluoromethyl, (e) monofluoromethyl, (f) methyl ketone, (g) trifluoromethyl ketone, (h) difluoromethyl ketone, (i) monofluoromethyl ketone, (j) formyl, (k) methyl alcohol, (l) methylamine, or (m) a bond; X is either a heterocycloalkyl-carbonyl-L-glutamate group, a heterocycloaryl-carbonyl-L-glutamate group, or a hydrogen (H), and wherein X is a hydrogen then $R_4$ is a heterocycloalkyl-carbonyl-L-glutamate group or a heterocycloaryl-carbonyl-L-glutamate group, and wherein X is a heterocycloalkyl-carbonyl-L-glutamate group or a heterocycloaryl-carbonyl-L-glutamate group, then $R_4$ is a hydrogen or a bond; wherein $R_5$ is the same as $R_3$ except that $R_5$ is not a bond; y is an integer ranging from zero up to and including 6; z is an integer ranging from zero up to and including seven, wherein the sum total of integers y and z is equal to or less than seven.

Another embodiment of this invention comprises the compound of Formula I, as described herein, wherein the side chain attachment is at carbon atom position 6 and wherein A is CR'R'', and wherein the carbon atom at position 5, independently, has attached thereto either (a) two hydrogen atoms if the bond between carbon atoms at positions 5 and 6 is a single bond or one hydrogen atom if the bond between carbon atoms at positions 5 and 6 is a double bond, or (b) an alkyl group having from one to six carbon atoms if the bond between carbon atoms of positions 5 and 6 is a double bond or an alkyl group having from one to six carbon atoms and a hydrogen atom if the bond between carbon atoms at positions 5 and 6 is a single bond, and combinations thereof.

In another embodiment of this invention, the compound of Formula I, as described herein, is provided comprising wherein the side chain attachment is at carbon atom position 6 and wherein A is NR' wherein R' is either a hydrogen atom or an alkyl group having from one to six carbon atoms, and wherein the carbon atom at position 5, independently, has attached thereto either (a) two hydrogen atoms if the bond between carbon atoms at positions 5 and 6 is a single bond or one hydrogen atom if the bond between carbon atoms at positions 5 and 6 is a double bond, or (b) an alkyl group having from one to six carbon atoms if the bond between carbon atoms of positions 5 and 6 is a double bond or an alkyl group having from one to six carbon atoms and a hydrogen atom if the bond between carbon atoms at positions 5 and 6 is a single bond, and combinations thereof.

In yet another embodiment of this invention, a compound of Formula I, as described herein, is provided comprising wherein said side chain attachment is at carbon atom position 5 and wherein and wherein A is CR'R'', and wherein the carbon atom at position 6, independently, has attached thereto either (a) two hydrogen atoms if the bond between carbon atoms at positions 5 and 6 is a single bond or one hydrogen atom if the bond between carbon atoms at positions 5 and 6 is a double bond, or (b) an alkyl group having from one to six carbon atoms if the bond between carbon atoms of positions 5 and 6 is a double bond or an alkyl group having from one to six carbon atoms and a hydrogen atom if the bond between carbon atoms at positions 5 and 6 is a single bond, and combinations thereof.

Another embodiment of this invention provides a compound of Formula I, as described herein, comprising wherein the side chain attachment is at carbon atom position 5 and wherein A is NR' wherein R' is either a hydrogen atom or an alkyl group having from one to six carbon atoms, and wherein the carbon atom at position 6, independently has attached thereto either (a) two hydrogen atoms if the bond between carbon atoms at positions 5 and 6 is a single bond or one hydrogen atom if the bond between carbon atoms at positions 5 and 6 is a double bond, or (b) an alkyl group having from one to six carbon atoms if the bond between carbon atoms of positions 5 and 6 is a double bond or an alkyl group having from one to six carbon atoms and a hydrogen atom if the bond between carbon atoms at positions 5 and 6 is a single bond, and combinations thereof.

In another embodiment of this invention, the compound of Formula I, as described herein, comprises the side chain having one or more carbon to carbon double or triple bonds between the carbon atoms of $(C)_y$ and $(C)_z$.

In a preferred embodiment of this invention, the compound of Formula I, as described herein, is provided comprising wherein A is NR' and R' is a hydrogen atom, and wherein y is from one to six carbon atoms, z is zero, $R_3$, and $R_5$ are each hydrogen atoms, and X is selected from the group consisting of a heterocycloalkyl-carbonyl-L-glutamate group and a heterocycloaryl-carbonyl-L-glutamate group. The heterocycloalkyl-carbonyl-L-glutamate group is selected from the group consisting of a dihydrothiophene-carbonyl-L-glutamate group, a tetrahydrothiophene-carbonyl-L-glutamate group, a dihydrofuran-carbonyl-L-glutamate group, a tetrahydrofuran-carbonyl-L-glutamate group, a dihydropyrrole-carbonyl-L-glutamate group, a tetrahydropyrrole-carbonyl-L-glutamate group, a monohydropyridyl-carbonyl-L-glutamate group, a dihydropyridyl-carbonyl-L-glutamate group, and a piperidyl-carbonyl-L-glutamate group, and stereoisomers thereof. The heterocycloaryl-carbonyl-L-glutamate group is selected from the group consisting of a thiophene-carbonyl-L-glutamate group, a furan-carbonyl-L-glutamate group, a pyrrole-carbonyl-L-glutamate group, and a pyridine-carbonyl-L-glutamate group.

In another embodiment of this invention, the compound of Formula I, as described herein, provides wherein the side chain of Formula I comprises zero or one or more double bonds comprising E-isomers and Z-isomers.

Other embodiments of this invention provide for the R and S optical isomers of the heterocyclic compounds of the present invention when the double bond of the ring system is broken.

Other embodiments of this invention provide a pharmaceutical composition having a therapeutically effective amount of a compound comprising Formula I, and a pharmaceutically acceptable salt, prodrug, solvate or hydrate of the compound comprising Formula I, as described herein.

Further embodiments of this invention provide methods for treating cancer, targeting cancerous cells via the proton coupled folate transporter pathway, inhibiting GARFTase in cancerous cells, and selectively targeting activated macrophages in a patient having an autoimmune disease, such as rheumatoid arthritis.

A preferred embodiment of the present invention provides for a compound comprising Formula II:

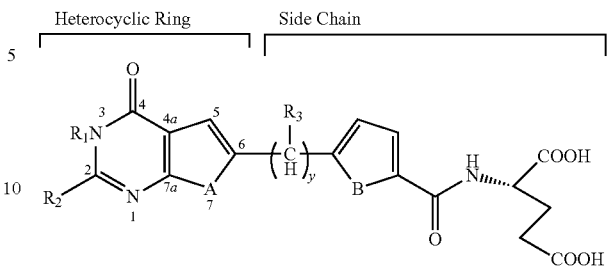

(II)

wherein $R_1$ comprises one of a hydrogen (H) or an alkyl group having from 1 to 6 carbon atoms;

$R_2$ comprises one of (a) a hydrogen (H), (b) a $CH_3$, (c) an OH, and (d) NHR wherein R is either a H or an alkyl group having from 1 to 6 carbon atoms;

A comprises one of (a) CR'R", (b) NR', wherein R' and R" are the same or different and are either a H or an alkyl group having from 1 to 6 carbon atoms, (c) a sulfur (S), and (d) an oxygen (O);

wherein the bond at position 5-6 is a double bond;

wherein the five membered ring has a side chain attached at position 6, and optionally includes wherein the carbon atoms at positions 5 and 6, independently, have attached thereto either (a) one hydrogen atom, or (b) an alkyl group having from one to six carbon atoms, and combinations thereof; and $R_3$ comprises one of (a) a hydrogen (H), (b) $CH_3$, (c) trifluoromethyl, (d) difluoromethyl, (e) monofluoromethyl, (f) methyl ketone, (g) trifluoromethyl ketone, (h) difluoromethyl ketone, (i) monofluoromethyl ketone, (j) formyl, (k) methyl alcohol, (l) methylamine, or (m) a bond;

B is one of (a) a sulfur (S) atom, (b) an oxygen (O) atom, or (c) a nitrogen (N) atom; and y is an integer ranging from zero up to and including 7.

Another embodiment of this invention provides the compound of Formula II comprising wherein the side chain has one or more carbon to carbon double or triple bonds between the carbon atoms of $(C)_{y, 1-7}$. In another embodiment of this invention the compound of Formula II comprises wherein the side chain comprises zero or one or more double bonds comprising E-isomers and Z-isomers. Another embodiment provides the compound of Formula II comprising one of a pharmaceutically acceptable salt, prodrug, solvate, or hydrate thereof. A pharmaceutical composition comprising a therapeutically effective amount of a compound of Formula II is also provided.

BRIEF DESCRIPTION OF THE DRAWINGS

A full understanding of the invention may be gained from the following description of the preferred embodiments of the when read in conjunction with the accompanying drawings in which:

FIG. 2 shows the biological effects of various compounds of the present invention.

DESCRIPTION OF THE PREFERRED EMBODIMENTS

Figure 1:
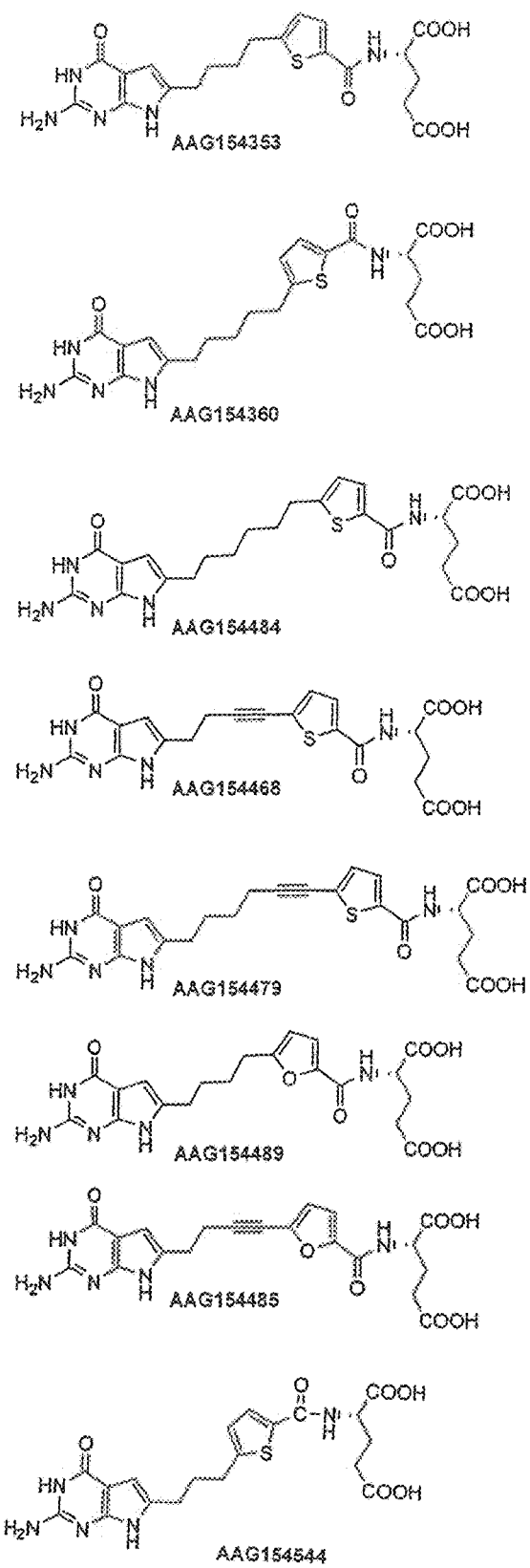
FIG. 1 shows the chemical structures of seven compounds of the present invention, namely, sample IDs AAG154353, AAG154360, AAG154484, AAG154468, AAG154479, AAG154489, AAG154485, and AAG154544.

The present invention provides a compound comprising Formula I:

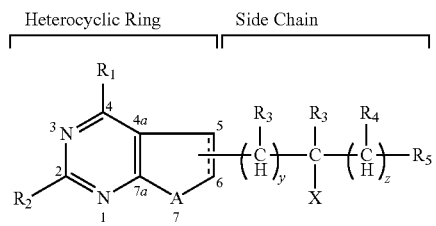

I wherein $R_1$ comprises one of (a) a hydrogen (H)), (b) an OH, (c) $CH_3$, and (d) NHR wherein R is either a H or an alkyl group having from 1 to 6 carbon atoms, and tautomers of (b) and (d); $R_2$ comprises one of (a) a hydrogen (H), (b) a $CH_3$, (c) an OH, and (d) NHR wherein R is either a H or an alkyl group having from 1 to 6 carbon atoms; A comprises one of (a) CR'R", (b) NR', wherein R' and R" are the same or different and are either a H or an alkyl group having from 1 to 6 carbon atoms, (c) a sulfur (S), and (d) an oxygen (O); wherein the bond at position 5-6 may either be a single or a double bond; wherein the five membered ring has a side chain attached at positions 5, 6 or 7, and wherein when said side chain attachment is at position 7 then A comprises one of (a) CR', and (b) N, and optionally includes wherein the carbon atoms at positions 5 and 6, independently, have attached thereto either (a) two hydrogen atoms if the bond between carbon atoms 5 and 6 is a single bond or one hydrogen atom if the bond between carbon atoms 5 and 6 is a double bond, or (b) an alkyl group having from one to six carbon atoms and a hydrogen atom if the bond between carbon atoms at positions 5 and 6 is a single bond or an alkyl group having from one to six carbon atoms if the bond between carbon atoms 5 and 6 is a double bond, and combinations thereof; and $R_3$ comprises one of (a) a hydrogen (H), (b) $CH_3$, (c) trifluoromethyl, (d) difluoromethyl, (e) monofluoromethyl, (f) methyl ketone, (g) trifluoromethyl ketone, (h) difluoromethyl ketone, (i) monofluoromethyl ketone, (j) formyl, (k) methyl alcohol, (l) methylamine, or (m) a bond; X is either a heterocycloalkyl-carbonyl-L-glutamate group, a heterocycloaryl-carbonyl-L-glutamate group, or a hydrogen (H), and wherein X is a hydrogen then $R_4$ is a heterocycloalkyl-carbonyl-L-glutamate group or a heterocycloaryl-carbonyl-L-glutamate group, and wherein X is a heterocycloalkyl-carbonyl-L-glutamate group or a heterocycloaryl-carbonyl-L-glutamate group then $R_4$ is a hydrogen or a bond; wherein $R_5$ is the same as $R_3$ except that $R_5$ is not a bond; y is an integer ranging from zero up to and including 6; z is an integer ranging from zero up to and including seven, wherein the sum total of integers y and z is equal to or less than seven.

Another embodiment of this invention comprises the compound of Formula I, as described herein, wherein the side chain attachment is at carbon atom position 6 and wherein A is the CR'R", and wherein the carbon atom at position 5, independently has attached thereto either (a) two hydrogen atoms if the bond between carbon atoms at positions 5 and 6 is a single bond or one hydrogen atom if the bond between carbon atoms at positions 5 and 6 is a double bond, or (b) an alkyl group having from one to six carbon atoms if the bond between carbon atoms of positions 5 and 6 is a double bond or an alkyl group having from one to six carbon atoms and a hydrogen atom if the bond between carbon atoms at positions 5 and 6 is a single bond, and combinations thereof.

In another embodiment of this invention, the compound of Formula I, as described herein, is provided comprising wherein the side chain attachment is at carbon atom position 6 and wherein A is NR' wherein R' is either a hydrogen atom or an alkyl group having from one to six carbon atoms, and wherein the carbon atom at position 5, independently has attached thereto either (a) two hydrogen atoms if the bond between carbon atoms at positions 5 and 6 is a single bond or one hydrogen atom if the bond between carbon atoms at positions 5 and 6 is a double bond, or (b) an alkyl group having from one to six carbon atoms if the bond between carbon atoms of positions 5 and 6 is a double bond or an alkyl group having from one to six carbon atoms and a hydrogen atom if the bond between carbon atoms at positions 5 and 6 is a single bond, and combinations thereof.

In yet another embodiment of this invention, a compound of Formula I, as described herein, is provided comprising wherein said side chain attachment is at carbon atom position 5 and wherein and wherein A is the CR'R", and wherein the carbon atom at position 6, independently has attached thereto either (a) two hydrogen atoms if the bond between carbon atoms at positions 5 and 6 is a single bond or one hydrogen atom if the bond between carbon atoms at positions 5 and 6 is a double bond, or (b) an alkyl group having from one to six carbon atoms if the bond between carbon atoms of positions 5 and 6 is a double bond or an alkyl group having from one to six carbon atoms and a hydrogen atom if the bond between carbon atoms at positions 5 and 6 is a single bond, and combinations thereof.

Another embodiment of this invention provides a compound of Formula I, as described herein, comprising wherein the side chain attachment is at carbon atom position 5 and wherein A is NR' wherein R' is either a hydrogen atom or an alkyl group having from one to six carbon atoms, and wherein the carbon atom at position 6, independently has attached thereto either (a) two hydrogen atoms if the bond between carbon atoms at positions 5 and 6 is a single bond or one hydrogen atom if the bond between carbon atoms at positions 5 and 6 is a double bond, or (b) an alkyl group having from one to six carbon atoms if the bond between carbon atoms of positions 5 and 6 is a double bond or an alkyl group having from one to six carbon atoms and a hydrogen atom if the bond between carbon atoms at positions 5 and 6 is a single bond, and combinations thereof.

The heterocycloalkyl-carbonyl-L-glutamate group is selected from the group consisting of a dihydrothiophene-carbonyl-L-glutamate group, a tetrahydrothiophene-carbonyl-L-glutamate group, a dihydrofuran-carbonyl-L-glutamate group, a tetrahydrofuran-carbonyl-L-glutamate group, a dihydropyrrole-carbonyl-L-glutamate group, a tetrahydropyrrole-carbonyl-L-glutamate group, a monohydropyridyl-carbonyl-L-glutamate group, a dihydropyridyl-carbonyl-L-glutamate group, and a piperidyl-carbonyl-L-glutamate group, and stereoisomers thereof.

The heterocycloaryl-carbonyl-L-glutamate group is selected from the group consisting of a thiophene-carbonyl-L-glutamate group, a furan-carbonyl-L-glutamate group, a pyrrole-carbonyl-L-glutamate group, and a pyridine-carbonyl-L-glutamate group.

In another embodiment of this invention, the compound of Formula I, as described herein, comprises the side chain having one or more carbon to carbon double or triple bonds between the carbon atoms of $(C)_y$ and $(C)_z$.

In a preferred embodiment of this invention, the compound of Formula I, as described herein, is provided comprising wherein A is NR' and R' is a hydrogen atom, and wherein y is from one to six carbon atoms, z is zero, $R_3$, and $R_5$ are each hydrogen atoms, and X is selected from the group consisting of a heterocycloalkyl-carbonyl-L-glutamate group or a heterocycloaryl-carbonyl-L-glutamate group.

In another embodiment of this invention, the compound of Formula I, as described herein, provides wherein the side chain of Formula I comprises zero or one or more double bonds comprising E-isomers and Z-isomers.

Another embodiment of this invention provides a pharmaceutically acceptable salt, prodrug, solvate or hydrate of the compound of Formula I, as described herein.

In yet another embodiment of this invention, a pharmaceutical composition is provided comprising a therapeutically effective amount of a compound comprising Formula I:

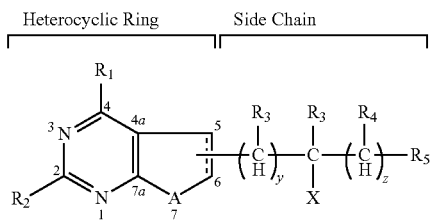

wherein $R_1$ comprises one of (a) a hydrogen (H)), (b) an OH, (c) $CH_3$, and (d) NHR wherein R is either a H or an alkyl group having from 1 to 6 carbon atoms, and tautomers of (b) and (d); $R_2$ comprises one of (a) a hydrogen (H), (b) a $CH_3$, (c) an OH, and (d) NHR wherein R is either a H or an alkyl group having from 1 to 6 carbon atoms; A comprises one of (a) CR'R", (b) NR', wherein R' and R" are the same or different and are either a H or an alkyl group having from 1 to 6 carbon atoms, (c) a sulfur (S), and (d) an oxygen (O); wherein the bond at position 5-6 may either be a single or a double bond; wherein the five membered ring has a side chain attached at positions 5, 6 or 7, and wherein when said side chain attachment is at position 7 then A comprises one of (a) CR', and (b) N, and optionally includes wherein the carbon atoms at positions 5 and 6, independently, have attached thereto either (a) two hydrogen atoms if the bond between carbon atoms 5 and 6 is a single bond or one hydrogen atom if the bond between carbon atoms 5 and 6 is a double bond, or (b) an alkyl group having from one to six carbon atoms and a hydrogen atom if the bond between carbon atoms at positions 5 and 6 is a single bond or an alkyl group having from one to six carbon atoms if the bond between carbon atoms 5 and 6 is a double bond, and combinations thereof; and $R_3$ comprises one of (a) a hydrogen (H), (b) $CH_3$, (c) trifluoromethyl, (d) difluoromethyl, (e) monofluoromethyl, (f) methyl ketone, (g) trifluoromethyl ketone, (h) difluoromethyl ketone, (i) monofluoromethyl ketone, (j) formyl, (k) methyl alcohol, (l) methylamine, or (m) a bond; X is either a heterocycloalkyl-carbonyl-L-glutamate group or a heterocycloaryl-carbonyl-L-glutamate group or a hydrogen (H), and wherein X is a hydrogen then $R_4$ is a heterocycloalkyl-carbonyl-L-glutamate group or a heterocycloaryl-carbonyl-L-glutamate group, and wherein X is a heterocycloalkyl-carbonyl-L-glutamate group or a heterocycloaryl-carbonyl-L-glutamate group then $R_4$ is a hydrogen or a bond; wherein $R_5$ is the same as $R_3$ except that $R_5$ is not a bond; y is an integer ranging from zero up to and including 6; z is an integer ranging from zero up to and including seven, wherein the sum total of integers y and z is equal to or less than seven.

In another embodiment of this invention, the pharmaceutical composition comprises wherein the side chain attachment is at carbon atom position 6 and wherein A is CR'R", and further comprising wherein the carbon atom at position 5, independently has attached thereto either (a) two hydrogen atoms if the bond between carbon atoms at positions 5 and 6 is a single bond or one hydrogen atom if the bond between carbon atoms at positions 5 and 6 is a double bond, or (b) an alkyl group having from one to six carbon atoms if the bond between carbon atoms of positions 5 and 6 is a double bond or an alkyl group having from one to six carbon atoms and a hydrogen atom if the bond between carbon atoms at positions 5 and 6 is a single bond, and combinations thereof.

In another embodiment of this invention, the pharmaceutical composition of Formula I comprises wherein the side chain attachment is at carbon atom position 6 and wherein A is NR' wherein R' is either a hydrogen atom or an alkyl group having from one to six carbon atoms, and wherein the carbon atom at position 5, independently has attached thereto either (a) two hydrogen atoms if the bond between carbon atoms at positions 5 and 6 is a single bond or one hydrogen atom if the bond between carbon atoms at positions 5 and 6 is a double bond, or (b) an alkyl group having from one to six carbon atoms if the bond between carbon atoms of positions 5 and 6 is a double bond or an alkyl group having from one to six carbon atoms and a hydrogen atom if the bond between carbon atoms at positions 5 and 6 is a single bond, and combinations thereof.

Another embodiment of this invention provides the pharmaceutical composition of Formula I comprising wherein the side chain attachment is at carbon atom position 5 and wherein and wherein A is CR'R", and further comprising wherein the carbon atom at position 6, independently has attached thereto either (a) two hydrogen atoms if the bond between carbon atoms at positions 5 and 6 is a single bond or one hydrogen atom if the bond between carbon atoms at positions 5 and 6 is a double bond, or (b) an alkyl group having from one to six carbon atoms if the bond between carbon atoms of positions 5 and 6 is a double bond or an alkyl group having from one to six carbon atoms and a hydrogen atom if the bond between carbon atoms at positions 5 and 6 is a single bond, and combinations thereof.

A further embodiment of this invention provides the pharmaceutical composition of Formula I comprising wherein the side chain attachment is at carbon atom position 5 and wherein A is NR' wherein R' is either a hydrogen atom or an alkyl group having from one to six carbon atoms, and wherein the carbon atom at position 6, independently has attached thereto either (a) two hydrogen atoms if the bond between carbon atoms at positions 5 and 6 is a single bond or one hydrogen atom if the bond between carbon atoms at positions 5 and 6 is a double bond, or (b) an alkyl group having from one to six carbon atoms if the bond between carbon atoms of positions 5 and 6 is a double bond or an alkyl group having from one to six carbon atoms and a hydrogen atom if the bond between carbon atoms at positions 5 and 6 is a single bond, and combinations thereof.

Another embodiment of this invention provides the pharmaceutical composition of Formula I comprising the side chain having one or more carbon to carbon double or triple bonds between the carbon atoms of $(C)_y$ and $(C)_z$.

In a preferred embodiment of this invention, the pharmaceutical composition of Formula I comprises wherein A is NR' and R' is a hydrogen atom, and wherein y is from one to six carbon atoms, z is zero, $R_3$, and $R_5$ are each hydrogen atoms, and X is selected from the group consisting of a heterocycloalkyl-carbonyl-L-glutamate group and a heterocycloaryl-carbonyl-L-glutamate group.

In another embodiment of this invention, the pharmaceutical composition of Formula I comprises wherein said the side chain of Formula I comprises zero or one or more double bonds comprising E-isomers and Z-isomers.

This invention provides for a pharmaceutically acceptable salt, prodrug, solvate or hydrate of the pharmaceutical composition of Formula I, as described herein.

A method of treating a patient diagnosed with cancer is provided in this invention comprising administering to a patient a therapeutically effective amount of a compound of Formula I:

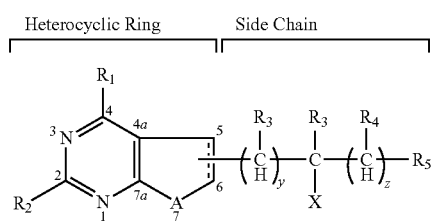

wherein $R_1$ comprises one of (a) a hydrogen (H)), (b) an OH, (c) $CH_3$, and (d) NHR wherein R is either a H or an alkyl group having from 1 to 6 carbon atoms, and tautomers of (b) and (d); $R_2$ comprises one of (a) a hydrogen (H), (b) a $CH_3$, (c) an OH, and (d) NHR wherein R is either a H or an alkyl group having from 1 to 6 carbon atoms; A comprises one of (a) CR'R", (b) NR', wherein R' and R" are the same or different and are either a H or an alkyl group having from 1 to 6 carbon atoms, (c) a sulfur (S), and (d) an oxygen (O); wherein the bond at position 5-6 may either be a single or a double bond; wherein the five membered ring has a side chain attached at positions 5, 6 or 7, and wherein when said side chain attachment is at position 7 then A comprises one of (a) CR', and (b) N, and optionally includes wherein the carbon atoms at positions 5 and 6, independently, have attached thereto either (a) two hydrogen atoms if the bond between carbon atoms 5 and 6 is a single bond or one hydrogen atom if the bond between carbon atoms 5 and 6 is a double bond, or (b) an alkyl group having from one to six carbon atoms and a hydrogen atom if the bond between carbon atoms at positions 5 and 6 is a single bond or an alkyl group having from one to six carbon atoms if the bond between carbon atoms 5 and 6 is a double bond, and combinations thereof; and $R_3$ comprises one of (a) a hydrogen (H), (b) $CH_3$, (c) trifluoromethyl, (d) difluoromethyl, (e) monofluoromethyl, (f) methyl ketone, (g) trifluoromethyl ketone, (h) difluoromethyl ketone, (i) monofluoromethyl ketone, (j) formyl, (k) methyl alcohol, (l) methylamine, or (m) a bond; X is either a heterocycloalkyl-carbonyl-L-glutamate group, a heterocycloaryl-carbonyl-L-glutamate group, or a hydrogen (H), and wherein X is a hydrogen then $R_4$ is a heterocycloalkyl-carbonyl-L-glutamate group or a heterocycloaryl-carbonyl-L-glutamate group, and wherein X is a heterocycloalkyl-carbonyl-L-glutamate group or a heterocycloaryl-carbonyl-L-glutamate group then $R_4$ is a hydrogen or a bond; wherein $R_5$ is the same as $R_3$ except that $R_5$ is not a bond; y is an integer ranging from zero up to and including 6; and z is an integer ranging from zero up to and including seven, wherein the sum total of integers y and z is equal to or less than seven.

In another embodiment of this invention, the method of treating a patient with cancer, as described herein, includes administering to the patient a compound of Formula I comprising wherein the side chain attachment is at carbon atom position 6 and wherein A is CR'R", and further comprising wherein the carbon atom at position 5, independently has attached thereto either (a) two hydrogen atoms if the bond between carbon atoms at positions 5 and 6 is a single bond or one hydrogen atom if the bond between carbon atoms at positions 5 and 6 is a double bond, or (b) an alkyl group having from one to six carbon atoms if the bond between carbon atoms of positions 5 and 6 is a double bond or an alkyl group having from one to six carbon atoms and a hydrogen atom if the bond between carbon atoms at positions 5 and 6 is a single bond, and combinations thereof.

Another embodiment of this invention provides a method of treating a patient with cancer, as described herein, including administering to the patient a compound of Formula I comprising wherein the side chain attachment is at carbon atom position 6 and wherein A is NR' wherein R' is either a hydrogen atom or an alkyl group having from one to six carbon atoms, and wherein the carbon atom at position 5, independently has attached thereto either (a) two hydrogen atoms if the bond between carbon atoms at positions 5 and 6 is a single bond or one hydrogen atom if the bond between carbon atoms at positions 5 and 6 is a double bond, or (b) an alkyl group having from one to six carbon atoms if the bond between carbon atoms of positions 5 and 6 is a double bond or an alkyl group having from one to six carbon atoms and a hydrogen atom if the bond between carbon atoms at positions 5 and 6 is a single bond, and combinations thereof.

In another embodiment of this invention, a method of treating a patient with cancer, as described herein, includes administering to the patient a compound of Formula I wherein the side chain attachment is at carbon atom position 5 and wherein A is CR'R", and further comprising wherein the carbon atom at position 6, independently has attached thereto either (a) two hydrogen atoms if the bond between carbon atoms at positions 5 and 6 is a single bond or one hydrogen atom if the bond between carbon atoms at positions 5 and 6 is a double bond, or (b) an alkyl group having from one to six carbon atoms if the bond between carbon atoms of positions 5 and 6 is a double bond or an alkyl group having from one to six carbon atoms and a hydrogen atom if the bond between carbon atoms at positions 5 and 6 is a single bond, and combinations thereof.

In another embodiment of this invention, a method of treating a patient with cancer, as described herein, includes administering to a patient a compound of Formula I wherein the side chain attachment is at carbon atom position 5 and wherein A is NR' wherein R' is either a hydrogen atom or an alkyl group having from one to six carbon atoms, and wherein the carbon atom at position 6, independently has attached thereto either (a) two hydrogen atoms if the bond between carbon atoms at positions 5 and 6 is a single bond or one hydrogen atom if the bond between carbon atoms at positions 5 and 6 is a double bond, or (b) an alkyl group having from one to six carbon atoms if the bond between carbon atoms of positions 5 and 6 is a double bond or an alkyl group having from one to six carbon atoms and a hydrogen atom if the bond between carbon atoms at positions 5 and 6 is a single bond, and combinations thereof.

The methods of treating a patient with cancer, as described herein, include wherein the heterocycloalkyl-carbonyl-L-glutamate group is selected from the group consisting of a dihydrothiophene-carbonyl-L-glutamate group, a tetrahydrothiophene-carbonyl-L-glutamate group, a dihydrofuran-carbonyl-L-glutamate group, a tetrahydrofuran-carbonyl-L-glutamate group, a dihydropyrrole-carbonyl-L-glutamate group, a tetrahydropyrrole-carbonyl-L-glutamate group, a monohydropyridyl-carbonyl-L-glutamate group, a dihydropyridyl-carbonyl-L-glutamate group, and a piperidyl-carbonyl-L-glutamate group, and stereoisomers thereof, and wherein the heterocycloaryl-carbonyl-L-glutamate group is selected from the group consisting of a thiophene-carbonyl-L-glutamate group, a furan-carbonyl-L-glutamate group, a pyrrole-carbonyl-L-glutamate group, and a pyridine-carbonyl-L-glutamate group.

The methods of treating a patient with cancer, as described herein, include administering to the patient an effective amount of the compound of Formula I wherein the side chain has one or more carbon to carbon double or triple bonds between the carbon atoms of $(C)_y$ and $(C)_z$.

Preferably, the method of treating a patient with cancer, as described herein, includes administering to the patient an effective amount of the compound of Formula I wherein A is NR' and R' is a hydrogen atom, and wherein y is from one to six carbon atoms, z is zero, $R_3$, and $R_5$ are each hydrogen atoms, and X is selected from the group consisting of a heterocycloalkyl-carbonyl-L-glutamate group or a heterocycloaryl-carbonyl-L-glutamate group, as described herein. The method of treating a patient with cancer, as described herein, includes administering to the patient an effective amount of a compound of Formula I wherein the side chain of Formula I comprises zero or one or more double bonds comprising E-isomers and Z-isomers.

All of the methods of treating a patient with cancer, as described herein, include administering to the patient an effective amount of the Compound of Formula I, as described herein, or a pharmaceutically acceptable salt, prodrug, solvate or hydrate of the compound. of Formula I, as described herein.

A method for targeting cancerous cells via the proton coupled folate transporter pathway is provided comprising:
(a) providing a compound comprising Formula I:

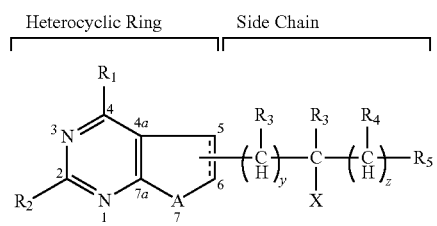

I wherein $R_1$ comprises one of (a) a hydrogen (H)), (b) an OH, (c) $CH_3$, and (d) NHR wherein R is either a H or an alkyl group having from 1 to 6 carbon atoms, and tautomers of (b) and (d);

$R_2$ comprises one of (a) a hydrogen (H), (b) a $CH_3$, (c) an OH, and (d) NHR wherein R is either a H or an alkyl group having from 1 to 6 carbon atoms;

A comprises one of (a) CR'R", (b) NR', wherein R' and R" are the same or different and are either a H or an alkyl group having from 1 to 6 carbon atoms, (c) a sulfur (S), and (d) an oxygen (O);

wherein the bond at position 5-6 may either be a single or a double bond;

wherein the five membered ring has a side chain attached at positions 5, 6 or 7, and wherein when said side chain attachment is at position 7 then A comprises one of (a) CR', and (b) N, and optionally includes wherein the carbon atoms at positions 5 and 6, independently, have attached thereto either (a) two hydrogen atoms if the bond between carbon atoms 5 and 6 is a single bond or one hydrogen atom if the bond between carbon atoms 5 and 6 is a double bond, or (b) an alkyl group having from one to six carbon atoms and a hydrogen atom if the bond between carbon atoms at positions 5 and 6 is a single bond or an alkyl group having from one to six carbon atoms if the bond between carbon atoms 5 and 6 is a double bond, and combinations thereof, and $R_3$ comprises one of (a) a hydrogen (H), (b) $CH_3$, (c) trifluoromethyl, (d) difluoromethyl, (e) monofluoromethyl, (f) methyl ketone, (g) trifluoromethyl ketone, (h) difluoromethyl ketone, (i) monofluoromethyl ketone, (j) formyl, (k) methyl alcohol, (l) methylamine, or (m) a bond;

X is either a heterocycloalkyl-carbonyl-L-glutamate group, a heterocycloaryl-carbonyl-L-glutamate group, or a hydrogen (H), and wherein X is a hydrogen then $R_4$ is a heterocycloalkyl-carbonyl-L-glutamate group or a heterocycloaryl-carbonyl-L-glutamate group, and wherein X is a heterocycloalkyl-carbonyl-L-glutamate group or a heterocycloaryl-carbonyl-L-glutamate group then $R_4$ is a hydrogen or a bond;

wherein $R_5$ is the same as $R_3$ except that $R_5$ is not a bond;
y is an integer ranging from zero up to and including 6;
z is an integer ranging from zero up to and including seven, wherein the sum total of integers y and z is equal to or less than seven;

(b) subjecting cancerous cells expressing a human proton coupled folate transporter (PCFT) to said compound of Formula I;

(c) establishing selective binding of said compound of Formula I to said human PCFT; and (d) effecting the selective transport of said compound of Formula I bound to said human PCFT to a target cancerous cell wherein said compound of Formula I acts as a growth inhibitor of said target cancerous cells and inhibits GARFTase within said target cancerous cells.

Another embodiment of this method for targeting cancerous cells of this invention, as described herein, include wherein the compound of Formula I is selective for receptors of FR alpha and human PCFT associated with expressing cancerous cells. In this method of targeting cancerous cell, the compound of Formula I is not significantly taken up by tissues or cells using the reduced folate carrier (RFC) system.

Other embodiments of this method for targeting cancerous cells comprise employing any of the various compounds of Formula I, or a pharmaceutically acceptable salt, prodrug, solvate or hydrate of a compound of Formula I, as described herein, thus it will be understood by those skilled in the art that any of the positions for attaching the side chain, as described herein, are embodiments of this invention. These methods for targeting cancer cells include wherein the compound targets cancerous cells selected from the group consisting of ovarian, breast, cervical, and kidney brain tumors.

A method for inhibiting GARFTase in cancerous cells is provided comprising:

(a) providing a compound of Formula I having a cytotoxic affect:

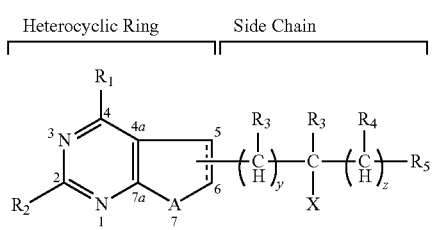

I wherein $R_1$ comprises one of (a) a hydrogen (H)), (b) an OH, (c) $CH_3$, and (d) NHR wherein R is either a H or an alkyl group having from 1 to 6 carbon atoms, and tautomers of (b) and (d);

$R_2$ comprises one of (a) a hydrogen (H), (b) a $CH_3$, (c) an OH, and (d) NHR wherein R is either a H or an alkyl group having from 1 to 6 carbon atoms;

A comprises one of (a) CR'R", (b) NR', wherein R' and R" are the same or different and are either a H or an alkyl group having from 1 to 6 carbon atoms, (c) a sulfur (S), and (d) an oxygen (O);

wherein the bond at position 5-6 may either be a single or a double bond;

wherein the five membered ring has a side chain attached at positions 5, 6 or 7, and wherein when said side chain attachment is at position 7 then A comprises one of (a) CR', and (b) N, and optionally includes wherein the carbon atoms at positions 5 and 6, independently, have attached thereto either (a) two hydrogen atoms if the bond between carbon atoms 5 and 6 is a single bond or one hydrogen atom if the bond between carbon atoms 5 and 6 is a double bond, or (b) an alkyl group having from one to six carbon atoms and a hydrogen atom if the bond between carbon atoms at positions 5 and 6 is a single bond or an alkyl group having from one to six carbon atoms if the bond between carbon atoms 5 and 6 is a double bond, and combinations thereof, and $R_3$ comprises one of (a) a hydrogen (H), (b) $CH_3$, (c) trifluoromethyl, (d) difluoromethyl, (e) monofluoromethyl, (f) methyl ketone, (g) trifluoromethyl ketone, (h) difluoromethyl ketone, (i) monofluoromethyl ketone, (j) formyl, (k) methyl alcohol, (l) methylamine, or (m) a bond;

X is either a heterocycloalkyl-carbonyl-L-glutamate group, a heterocycloaryl-carbonyl-L-glutamate group, or a hydrogen (H), and wherein X is a hydrogen then $R_4$ is a heterocycloalkyl-carbonyl-L-glutamate group or a heterocycloaryl-carbonyl-L-glutamate group, and wherein X is a heterocycloalkyl-carbonyl-L-glutamate group or a heterocycloaryl-carbonyl-L-glutamate group then $R_4$ is a hydrogen or a bond;

wherein $R_5$ is the same as $R_3$ except that $R_5$ is not a bond; y is an integer ranging from zero up to and including 6; z is an integer ranging from zero up to and including seven, wherein the sum total of integers y and z is equal to or less than seven;

(b) selectively delivering said compound to said cancerous cell;

(c) effecting the entry of said compound into said cancerous cell;

(d) retaining said compound in said cancerous cell for a sufficient amount of time for effecting binding of said compound with a GARFTase enzyme; and (e) lysing of said cancerous cell via said binding of said compound with said GARFTase enzyme and inhibiting the DNA replication of said cancerous cell.

Preferably, the method, of this invention, of inhibiting GARFTase, as described herein, comprises wherein the compound of Formula I or a pharmaceutically acceptable salt, prodrug, solvate or hydrate of the compound of Formula I is selective for receptors of FR alpha associated with expressing cancerous cells.

Other embodiments of this invention of inhibiting GARTase, as described herein, include employing any one of the various embodiments of the compound of Formula I or its pharmaceutically acceptable salt, prodrug, solvate or hydrate, as described herein, including comprising the side chain attachment at various positions 5, 6 or 7, as described herein.

Another embodiment of this invention provides for the inhibition of AICARFTase when A is equal to a sulfur atom in the compound of Formula I.

Rheumatoid arthritis is an autoimmune disease that affects the quality of life of millions of patients worldwide. Rheumatoid arthritis is characterized by inflammation of a patient's joints and destruction of the cartilage and bone of the patient. While the pathology of rheumatoid arthritis is complex, it is known to involve the infiltration and activation of immune cells along with the release of destructive inflammatory mediators into a patient's synovium of affected joints. Paulos, Chrystal M., et al., "Folate receptor-mediated targeting of therapeutic and imaging agents to activated macrophages in rheumatoid arthritis", Advanced Drug Delivery Reviews, Vol. 56, pages 1205-1217 (2004), describe the discovery of folate receptor expression on activated macrophage cells in patient models (human and animal) with naturally occurring rheumatoid arthritis, and is incorporated herein by reference, specifically section 3, page 1208 and section 5, pages 1212-1214.

The present invention provides a method for selectively targeting activated macrophages in a patient having an autoimmune disease comprising:

(a) providing a compound comprising Formula I:

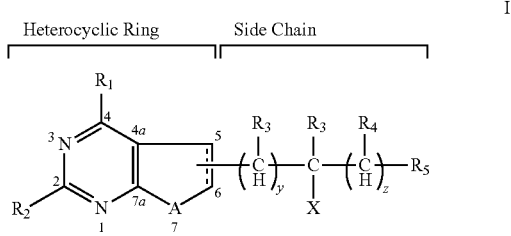

I wherein $R_1$ comprises one of (a) a hydrogen (H), (b) an OH, (c) $CH_3$, and (d) NHR wherein R is either a H or an alkyl group having from 1 to 6 carbon atoms, and tautomers of (b) and (d);

$R_2$ comprises one of (a) a hydrogen (H), (b) a $CH_3$, (c) an OH, and (d) NHR wherein R is either a H or an alkyl group having from 1 to 6 carbon atoms;

A comprises one of (a) CR'R", (b) NR', wherein R' and R" are the same or different and are either a H or an alkyl group having from 1 to 6 carbon atoms, (c) a sulfur (S), and (d) an oxygen (O);

wherein the bond at position 5-6 may either be a single or a double bond;

wherein the five membered ring has a side chain attached at positions 5, 6 or 7, and wherein when said side chain attachment is at position 7 then A comprises one of (a) CR', and (b) N, and optionally includes wherein the carbon atoms at positions 5 and 6, independently, have attached thereto either (a) two hydrogen atoms if the bond between carbon atoms 5 and 6 is a single bond or one hydrogen atom if the bond between carbon atoms 5 and 6 is a double bond, or (b) an alkyl group having from one to six carbon atoms and a hydrogen atom if the bond between carbon atoms at positions 5 and 6 is a single bond or an alkyl group having from one to six carbon atoms if the bond between carbon atoms 5 and 6 is a double bond, and combinations thereof, and $R_3$ comprises one of (a) a hydrogen (H), (b) $CH_3$, (c) trifluoromethyl, (d) difluoromethyl, (e) monofluoromethyl, (f) methyl ketone, (g) trifluoromethyl ketone, (h) difluoromethyl ketone, (i) monofluoromethyl ketone, (j) formyl, (k) methyl alcohol, (l) methylamine, or (m) a bond;

X is either a heterocycloalkyl-carbonyl-L-glutamate group, a heterocycloaryl-carbonyl-L-glutamate group, or a hydrogen (H), and wherein X is a hydrogen then $R_4$ is a heterocycloalkyl-carbonyl-L-glutamate group or a heterocycloaryl-carbonyl-L-glutamate group, and wherein X is a heterocycloalkyl-carbonyl-L-glutamate group or a heterocycloaryl-carbonyl-L-glutamate group then $R_4$ is a hydrogen or a bond;

wherein $R_5$ is the same as $R_3$ except that $R_5$ is not a bond;

y is an integer ranging from zero up to and including 6;

z is an integer ranging from zero up to and including seven, wherein the sum total of integers y and z is equal to or less than seven;

(b) subjecting an activated macrophage expressing a folate receptor (FR) to said compound of Formula I;

(c) establishing selective binding of said compound of Formula I to said FR; and (d) effecting the selective transport of said compound of Formula I bound to said FR to a target activated macrophage of the autoimmune disease wherein said compound of Formula I acts as an inhibitor of said activated macrophage's release of destructive inflammatory mediators.

The method for selectively targeting activated macrophages of the present invention includes wherein the compound of Formula I is selective for receptors of FR alpha and human proton coupled folate transporter (PCFT) associated with expressing macrophage cells.

Preferably, the method for selectively targeting activated macrophages in a patient having an autoimmune disease, as described herein, includes wherein the activated macrophage cell expressing the FR is rheumatoid arthritis.

Other embodiments of the method for targeting activated macrophage cells in a patient with an autoimmune disease, include wherein the compound of Formula I, or its pharmaceutically acceptable salts, prodrugs, solvates or hydrates of the compound of Formula I, include any of the various embodiments, as described herein, of the compound of Formula I, including attachment of the side chain at any of the positions 5, 6, or 7, as described herein.

Preferably, the method of selectively targeting an activated macrophage in a patient having an autoimmune disease that is rheumatoid arthritis includes delivering the compound of Formula I or a pharmaceutically acceptable salt, prodrug, solvate or hydrate of the compound of Formula I by injection into a joint or synovial fluid of a patient.

A preferred embodiment of the present invention provides for a compound comprising Formula II:

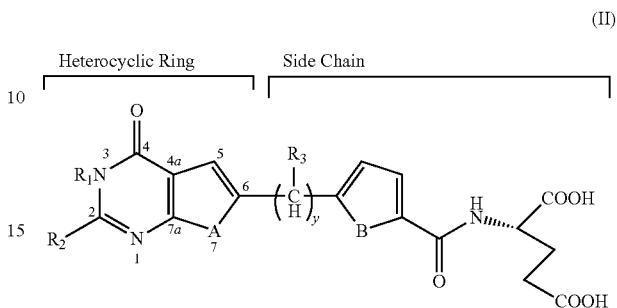

(II)

wherein $R_1$ comprises one of a hydrogen (H) or an alkyl group having from 1 to 6 carbon atoms;

$R_2$ comprises one of (a) a hydrogen (H), (b) a $CH_3$, (c) an OH, and (d) NHR wherein R is either a H or an alkyl group having from 1 to 6 carbon atoms;

A comprises one of (a) CR'R", (b) NR', wherein R' and R" are the same or different and are either a H or an alkyl group having from 1 to 6 carbon atoms, (c) a sulfur (S), and (d) an oxygen (O);

wherein the bond at position 5-6 is a double bond;

wherein the five membered ring has a side chain attached at position 6, and optionally includes wherein the carbon atoms at positions 5 and 6, independently, have attached thereto either (a) one hydrogen atom, or (b) an alkyl group having from one to six carbon atoms, and combinations thereof; and $R_3$ comprises one of (a) a hydrogen (H), (b) $CH_3$, (c) trifluoromethyl, (d) difluoromethyl, (e) monofluoromethyl, (f) methyl ketone, (g) trifluoromethyl ketone, (h) difluoromethyl ketone, (i) monofluoromethyl ketone, (j) formyl, (k) methyl alcohol, (l) methylamine, or (m) a bond;

B is one of (a) a sulfur (S) atom, (b) an oxygen (O) atom, or (c) a nitrogen (N) atom; and y is an integer ranging from zero up to and including 7.

Another embodiment of this invention provides the compound of Formula II comprising wherein the side chain has one or more carbon to carbon double or triple bonds between the carbon atoms of $(C)_{y\ 1-7}$. In another embodiment of this invention the compound of Formula II comprises wherein the side chain comprises zero or one or more double bonds comprising E-isomers and Z-isomers. Another embodiment provides the compound of Formula II comprising one of a pharmaceutically acceptable salt, prodrug, solvate, or hydrate thereof. A pharmaceutical composition comprising a therapeutically effective amount of a compound of Formula II is also provided. Other preferred embodiments of the present invention provide for methods as described herein for treating cancer, selectively targeting cancerous cells via the proton coupled folate transporter, folate receptor alpha, and/or folate receptor beta pathways, inhibiting GARFTase in cancerous cells, and selectively targeting activated macrophages in a patient having an autoimmune disease employing the compound of Formula II as the preferred tautomer provided by the compound of Formula I.

While the Formula II shows attachments of the five membered ring of the side chain to be at the 2 and 5 positions (numbering clockwise with "B" being at position 1), the substituents attached to the five membered ring of the side chain may be at various positions, including for example, at the 2 and 3 positions, at the 2 and 4 positions, at the 3 and 4 positions, and at the 3 and 5 positions.

As used herein, the term "patient" means members of the animal kingdom, including, but not limited to, human beings. As used herein, the term "having cancer" means that the patient has been diagnosed with cancer.

As used herein, the term "therapeutically effective amount" refers to that amount of any of the present compounds required to bring about a desired effect in a patient. The desired effect will vary depending on the illness being treated. For example, the desired effect may be reducing tumor size, destroying cancerous cells, and/or preventing metastasis, any one of which may be the desired therapeutic response. On its most basic level, a therapeutically effective amount is that amount needed to inhibit the mitosis of a cancerous cell.

Compounds of the present invention covered under Formula I or II, and pharmaceutically acceptable salts, prodrugs, solvates or hydrates thereof, may also be administered with one or more additional treatment agents, i.e., a chemotherapeutic agent. Suitable candidates for the additional chemotherapeutic agent include for example but are not limited to, paclitaxel, docetaxel, vinca alkaloids, colchicines, colcemid, cisplatin, and nocadazol.

As used herein, the term "lower alkyl" group refers to those lower alkyl groups having one to about ten carbon atoms, such as for example methyl, ethyl, propyl, butyl, pentyl, hexyl, cyclopropyl, cyclobutyl, cyclohexyl, cyclopropylmethyl or cyclobutylmethyl groups. Alkyl groups sharing one to about six carbon atoms are preferred. These lower alkyl groups are straight chain, branched chain or cyclic (alicyclic hydrocarbon) arrangements. The carbon atoms of these straight chain, branched chain or cyclic arranged alkyl groups may have one or more substituents for the hydrogens attached to the carbon atoms.

As used herein, the term "heteroalkyl" refers to alkyl chains from one to about 3 atoms where one or more of the carbons has been replaced with nitrogen, oxygen or sulfur, Thus "heteroalkyl" groups will include, for example, C—C—N, C—S, S—C, C—O, C—C—O, O—C, N—C—C, N—C—C and other various combinations, as will be apparent to one skilled in the art. The above list is not meant to be exhaustive, and many combinations are contemplated as within the scope of the present invention.

The term "aryl" groups, as used herein, refers to compounds whose molecules have an aromatic ring structure, such as the six-carbon ring of benzene, or multiple rings which are either fused or unfused, such as condensed six-carbon rings of other aromatic derivatives. The term "aryl" is also defined to include diaryl, triaryl and polyaryl groups, which would have two, three or more rings, respectively. Thus, suitable aryl groups would include, for example, phenyl, biphenyl, naphthyl, phenanthrene, anthracene groups and aryl oxyaryl groups. This list is not meant to be exhaustive, and any aryl group, as these terms are defined above and commonly understood in the art, are within the scope of the present invention.

The term "heteroaryl" refers to aromatic ring structures having at least one atom in the ring which is not carbon, such as oxygen, nitrogen or sulfur. "Heteroaryls" as used herein also refers to aromatic ring structures that are part of larger ring structures, such as two or three member ring systems, which may be fused or unfused, in which one of the rings is as described above. Thus, "heteroaryl" refers to ring systems in which one or more rings contain a heteroatom and one or more rings do not. It will be understood that this list is not meant to be exhaustive, and that any heteroaryl group, as these terms are defined above and commonly understood in the art, are within the scope of the present invention. The heteroaryl ring systems may be fused ring systems or unfused. Examples of heteroaryl ring systems include, for example but are not limited to, pyridine, quinoline, isoquinoloine, pyrrole, thiophenes, furans, imidazoles, and the like, as well as fused ring structures having rings of different sizes, such as benzofurans, indoles, purines, and the like.

Also included within the scope of the present invention are alicyclic groups, as that term is understood in the art, and heterocyclic groups. As used herein, the term "heterocyclic group" refers to non-aromatic cyclic substituents in which one or more members of the ring is not carbon, for example oxygen, sulfur or nitrogen.

The terms "alkylaryl" (or "alkaryl") or "alkylheteroaryl" as used herein refer to groups having an alkyl moiety attached to an aryl or heteroaryl ring. The alkyl moiety is preferably a straight, branched or cyclic alkyl group having one to about six carbon atoms. This alkyl moiety may also contain oxygen, nitrogen or sulfur, and therefore may be an alkoxy group. The aryl or heteroaryl moiety of the alkylaryl group is a substituted or unsubstituted aryl or heteroaryl group, as these terms are described above. As used herein, the terms "alkylaryl" or "alkylheteroaryl" will also be used to refer to arylalkyl groups or heteroarylalkyl groups, as those terms are understood in the art, and denotes attachment of such a substituent at either the alkyl or the aryl portion of the group. Thus, for example, a benzyl group would be embraced by the term "alkylaryl".

Any of the cyclic substituents described above, such as the aryl, heteroaryl, alkylaryl, alkylheteroaryl, alicyclic, or heterocyclic groups are optionally substituted with one or more substituents as listed above. In the case of more than one substituent, the substituents are independently selected. "Alkoxy groups" and "alkyl groups" include straight or branched chains having up to about ten members. "Halogen" refers to chlorine, bromine, iodine and fluorine. "Aryl and heteroaryl groups" are as described above. When a carboxylic acid is a substituent, it will be appreciated that the moiety represents an acid such as benzoic acid. As used herein, the term heterocycloaryl-carbonyl-L-glutamate group may include for example a thiophene-carbonyl-L-glutamate group, a furan-carbonyl-L-glutamate group, a pyrrole-carbonyl-L-glutamate group, and a pyridine-carbonyl-L-glutamate group, and the term heterocycloalkyl-carbonyl-L-glutamate group may include for example a dihydrothiophene-carbonyl-L-glutamate group, a tetrahydrothiophene-carbonyl-L-glutamate group, a dihydrofuran-carbonyl-L-glutamate group, a tetrahydrofuran-carbonyl-L-glutamate group, a dihydropyrrole-carbonyl-L-glutamate group, a tetrahydropyrrole-carbonyl-L-glutamate group, a monohydropyridyl-carbonyl-L-glutamate group, a dihydropyridyl-carbonyl-L-glutamate group, and a piperidyl-carbonyl-L-glutamate group, and stereoisomers thereof, as those terms are understood by one skilled in the art.

As used herein, the terms "aroyl" or "heteroaroyl", such as when used within the term p-aroyl-L-glutamate, refers to benzoyl, napthoyl, thiophenoyl, furophenoyl, pyrroyl, and any other "aroyl" or "heteroaroyl" as these terms are understood by one skilled in the art. "Aroyl" and "heteroaroyl" are generally defined in the art as an aromatic or heteroaromatic compound having a carbonyl moiety. As used herein, the term "glutamate" will be understood as representing both the ester form (glutamate) and the acid form (glutamic acid).

Those skilled in the art shall understand that chemical structure of Formula II is a preferred example of this invention and that Formula II is a tautomer of an embodiment of a compound of Formula I. Those skilled in the art understand that chemical structures are often drawn as one tautomeric form over another. This invention provides for several tautomeric forms as covered by the description of Formula I. The tautomeric forms taught by Formula I provide several structural embodiments that will be appreciated by those skilled in the art, such as for example the compounds having Formula II.

Proliferative diseases and/or disorders that may be treated according to the methods of the present invention include, without limitation, ovarian cancer, endometrial and cervical cancer, renal cancer, and breast cancer, and autoimmune diseases such as for example rheumatoid arthritis.

It is especially advantageous to formulate parenteral compositions in dosage unit form for ease of administration and uniformity of dosage. Dosage unit form as used herein refers to physically discrete units suited as unitary dosages for the patients being treated, each unit containing a predetermined quantity or effective amount of a compound of the present invention to produce the desired effect in association with a pharmaceutical carrier. The specification for the dosage unit forms of the invention are dictated by and directly dependent on the particular compound and the particular effect, or therapeutic response, that is desired to be achieved.

Compounds of Formula I or II, or pharmaceutically acceptable salts, prodrugs, solvates, or hydrates thereof, can be administered to a patient (an animal or human) via various routes including parenterally, orally or intraperitoneally. Parenteral administration includes the following routes that are outside the alimentary canal (digestive tract): intravenous; intramuscular; interstitial, intraarterial; subcutaneous; intraocular; intracranial; intraventricular; intrasynovial; transepithelial, including transdermal, pulmonary via inhalation, ophthalmic, sublingual and buccal; topical, including dermal, ocular, rectal, or nasal inhalation via insufflation or nebulization. Specific modes of administration shall depend on the indication. The selection of the specific route of administration and the dose regimen is to be adjusted or titrated by the clinician according to methods known to the clinician in order to obtain the optimal clinical response. The amount of compound to be administered is that amount which is therapeutically effective. The dosage to be administered to a patient shall depend on the characteristics of the patient being treated, including for example, but not limited to, the patient's age, weight, health, and types and frequency of concurrent treatment, if any, of any other chemotherapeutic agent(s), all of which is determined by the clinician as one skilled in the art.

Compounds of Formula I or II, or a pharmaceutically acceptable salt, prodrug, solvate or hydrate thereof, that are orally administered can be enclosed in hard or soft shell gelatin capsules, or compressed into tablets. Compounds also can be incorporated with an excipient and used in the form of ingestible tablets, buccal tablets, troches, capsules, sachets, lozenges, elixirs, suspensions, syrups, wafers and the like. Compounds of Formula I or II can be in the form of a powder or granule, a solution or suspension in an aqueous liquid or non-aqueous liquid, or in an oil-in-water emulsion.

The tablets, troches, pills, capsules and the like also can contain, for example, a binder, such as gum tragacanth, acacia, corn starch; gelating excipients, such as dicalcium phosphate; a disintegrating agent, such as corn starch, potato starch, alginic acid and the like; a lubricant, such as magnesium stearate; a sweetening agent, such as sucrose, lactose or saccharin; or a flavoring agent. When the dosage unit form is a capsule, it can contain, in addition to the materials described above, a liquid carrier. Various other materials can be present as coatings or to otherwise modify the physical form of the dosage unit. For example, tablets, pills, or capsules can be coated with shellac, sugar or both. A syrup or elixir can contain the active compound, sucrose as a sweetening agent, methyl and propylparabens as preservatives, a dye and flavoring. Any material used in preparing any dosage unit form should be pharmaceutically pure and substantially non-toxic. Additionally, the compounds of Formulas I, II, or a pharmaceutically acceptable salt, prodrug, solvate or hydrate of Formulas I or II, can be incorporated into sustained-release preparations and formulations.

The compounds of Formula I, II, or a pharmaceutically acceptable salt, prodrug, solvate or hydrate thereof, can be administered to the central nervous system, parenterally or intraperitoneally. Solutions of the compound as a free base or a pharmaceutically acceptable salt can be prepared in water mixed with a suitable surfactant, such as hydroxypropylcellulose. Dispersions also can be prepared in glycerol, liquid polyethylene glycols and mixtures thereof, and in oils. Under ordinary conditions of storage and use, these preparations can contain a preservative and/or antioxidants to prevent the growth of microorganisms or chemical degeneration.

The pharmaceutical forms suitable for injectable use include, without limitation, sterile aqueous solutions or dispersions and sterile powders for the extemporaneous preparation of sterile injectable solutions or dispersions. In all cases, the form must be sterile and must be fluid to the extent that easy syringability exists. It can be stable under the conditions of manufacture and storage and must be preserved against the contaminating action of microorganisms, such as bacteria and fungi.

Compounds of the present invention may be contained within, mixed with, or associated with, a suitable (acceptable) pharmaceutical carrier for administration to a patient according to the particular route of administration desired. Suitable or acceptable pharmaceutical carriers refer to any pharmaceutical carrier that will solubilize the compounds of the present invention and that will not give rise to incompatibility problems, and includes any and all solvents, dispersion media, coatings, antibacterial and antifungal agents, isotonic agents, absorption delaying agents, and the like. The use of such suitable or acceptable pharmaceutical carriers are well known by those skilled in the art. Preferred carriers include sterile water, physiologic saline, and five percent dextrose in water. Examples of other suitable or acceptable pharmaceutical carriers include, but are not limited to, ethanol, polyol (such as propylene glycol and liquid polyethylene glycol), suitable mixtures thereof, or vegetable oils. The proper fluidity can be maintained, for example, by the use of a coating, such as lecithin, by the maintenance of the required particle size (in the case of a dispersion) and by the use of surfactants. The prevention of the action of microorganisms can be brought about by various antibacterial and anti-fungal agents, for example, parabens, chlorobutanol, phenol, sorbic acid, thimerosal, and the like. In many cases, it will be preferable to include isotonic agents, for example, sugars or sodium chloride.

Sterile injectable solutions are prepared by incorporating a compound of Formula I or II in the required amount in the appropriate solvent with various of the other ingredients enumerated above, as required, followed by filtered sterilization. Generally, dispersions are prepared by incorporating the sterilized compound of Formula I or II into a sterile vehicle that contains the basic dispersion medium and any of the other ingredients from those enumerated above. In the case of sterile powders for the preparation of sterile injectable solutions, the preferred methods of preparation are vacuum drying and freeze drying.

Pharmaceutical compositions which are suitable for administration to the nose and buccal cavity include, without limitation, self-propelling and spray formulations, such as aerosol, atomizers and nebulizers.

The therapeutic compounds of Formula I or II, as described herein, can be administered to a patient alone or in combination with pharmaceutically acceptable carriers or as pharmaceutically acceptable salts, solvates or hydrates thereof, the proportion of which is determined by the solubility and chemical nature of the compound, chosen route of administration to the patient and standard pharmaceutical practice.

The present invention is more particularly described in the following non-limiting examples, which are intended to be illustrative only, as numerous modifications and variations therein will be apparent to those skilled in the art.

EXAMPLES

FIG. 2 shows the biological effects of various compounds of the present invention, namely, Samples: AAG 154353, AAG154360, AAG154484, AAG154468, AAG154479, and AAG154489. These compounds were evaluated for cytotoxicity towards assorted cell lines, namely, KB human tumor cells expressing FRs and RFC, PC43-10, and Chinese hamster ovary expressing RFC, and RT16 Chinese hamster ovary cells expressing FRs but no RFC. FIG. 2 shows the $IC_{50}$ of each of the Sample compounds of the present invention towards each cancer cell line. The $IC_{50}$ is the inhibitory concentration required to effectuate fifty percent inhibition of cell growth.

Compounds AAG154353, AAG154360, AAG154489 and AAG154468 are potent inhibitors of KB human tumor cells known to express high levels of folate receptor alpha (FRα) with values of 0.25, 3.4, 0.3 and 122 nM respectively (see FIG. 2). In addition, the compounds are potently inhibitory against RT16 cells that express FRα and D4 cells that express folate receptor beta (FRβ). All the compounds as anticipated were inactive against cells engineered to lack FRα or FRβ, such as PC43 (only RFC) and R2 cells that lack FRα or β, as well as RFC. These results show that compounds AAG154353, AAG154360, AAG145489 and AAG154468 are selectively inhibitory only against cells and tumor cells that express FRs.

Inhibitory effects of AAG154353 and AAG154360, as examples of the heteroaroyl side chain analogs of the compounds of the present invention of Formula I, on RFC transport and FR binding were also evaluated. The PC43 cells, (RFC containing cells) that express RFC only, were used and the ability of the compounds to inhibit [$^3$H] MTX (methotrexate) uptake. Both example compounds AAG154353 and AAG154360 had very poor inhibitory activity, <20%, showing that these compounds do not inhibit [$^3$H] MTX uptake in PC43 cells. In contrast, the evaluation of the FRα binding affinity compared to folic acid showed very high binding affinities with relative affinities similar to folic acid set to a value of 1 (see FIG. 2). Similar results were obtained with FRβ and show that the prototype analogs are selective for and are excellent substrates for FRα and FRβ.

In-Vivo Evaluation of Sample: AAG154353 in Advanced Tumor Xenograft

SCID female mice bearing advanced stage human KB cervical tumors as xenografts (xenograft tumors) were administered compound AAG154353 of the present invention intravenously at various doses and schedules.

Mice were maintained on a Folic Acid deficient diet (Harlan-Teklad Diet #00434; Madison, Wis.) exclusively for approximately three weeks at the start of treatment. Three mice bearing late stage KB tumor xenografts (446 to 650 mg at the start of treatment) were each treated on various dose/schedules with AAG154353 IV. In all three cases, tumors regressed completely. Thus, significant antitumor activity was detected. Toxicity as reflected in weight loss was modest.

Dose/schedules tested:
1) Q3dx4 does starting day 37; 750 mg/kg total dose—mouse tumor free for one month, 30 days;
2) Q2dx4 doses starting day 43; 500 mg/kg total dose—mouse with 63 mg tumor; tumor free up to day 60.
3) Q4dx3 doses starting day 48; 187.5 mg/kg total dose—mouse tumor free for one month, 30 days.

Figure 3:
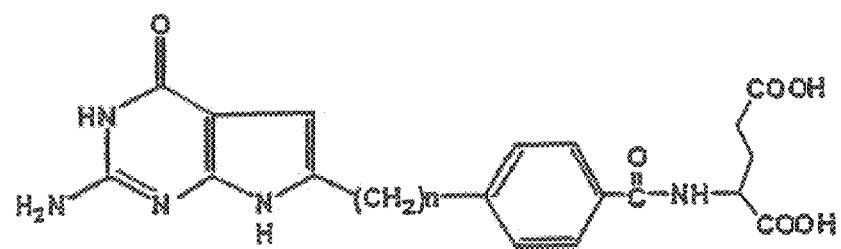
FIG. 3 shows the structure of a comparison compound AAG120366-2.

Description of FR and Human Proton-Coupled Folate Transporter (hPCFT) Studies with Pyrrolo[2,3-D]pyrimidine Antifolates Folate Receptor Studies:

Following the inventors' initial studies of pyrrolo[2,3-d]pyrimidine antifolates with 1 or 3 to 6 carbon bridge substitutions as represented by Compound AAG120366-2, structure shown in FIG. 3) to identify FR targeted agents with low level transport by human reduced folate carrier (hRFC) (Deng et al., 2008), we tested compounds of Formula I of the present invention, namely Example compounds AAG154353 and AAG154360, each having a thienoyl side chain in KB human tumor cells (see Table 1). The compounds AAG154353 and AAG154360 were initially tested for their growth inhibitory effects against KB human tumor cells, which express FR alpha and hRFC but insignificant levels human proton coupled folate transporter (hPCFT), using a fluorescence-based ("Cell Titer-blue") cytotoxicity screen. In KB cells, IC50s of 0.25 and 3.4 nM were measured from compounds AAG154353 and AAG154360. FR-targeted activity by AAG154353 and AAG154360 was confirmed by co-treatments with folic acid (200 nM) which completely reversed growth inhibition of these agents. AAG154353 and AAG154360 were also tested in isogenic Chinese hamster ovary (CHO) sublines, engineered to express human FR-(RT16) or hRFC (PC43-10). For PC43-10, results were compared to those for hRFC- and FR-null R2 CHO cells from which they were derived, whereas those for RT16 cells were compared to those for a parallel incubation in the presence of an elevated concentration of folic acid, as with the KB cells. AAG154353 and AAG154360 showed a high level of FR-targeted activity toward RT16 cells. Neither AAG154353 and AAG154360 showed appreciable growth inhibition of hRFC-expressing PC43-10 cells. These results are summarized in Table 1.

TABLE 1

IC50s (nM) for antifolate analogs in cell proliferation inhibition of RFC- and FR-expressing cell lines and results of in vitro and in situ GARFTase assays.

| | Growth inhibition (IC50, nM) | | | | | | GARFTase Assay | |
|---|---|---|---|---|---|---|---|---|
| | hRFC | | hFRα RT16 | | hRFC/FRα KB | | In vitro | In situ |
| Antifolate | PC43-10 | R2 | RT16 | (+FA) | KB | (+FA) | IC50 (µM) | IC50(nM) |
| AAG1203662 | 304 | 448 | 4.1 | >1000 | 1.7 | >1000 | 2.44 (0.12) | 18 (2) |
| AAG154353 | >1000 | >1000 | 2 | >1000 | 0.25 | >1000 | 0.06 (0.004) | 0.63 (0.52) |
| AAG154360 | >1000 | >1000 | 2 | >1000 | 3.4 | >1000 | 3.31 (0.32) | 7.65 (3.7) |
| Methotrexate | 12 | 216 | 114 | 461 | 6.0 | 20 | — | — |
| Pemetrexed | 138 | 894 | 42 | 388 | 68 | 327 | >20 | 30 (7.7) |
| Raltitexed | 6.3 | >1000 | 15 | >1000 | 5.9 | 22 | — | — |
| Lometrexol | 12 | >1000 | 12 | 188 | 1.2 | 31 | 0.78 (0.08) | 14 (5.6) |
| Trimetrexate | 25 | 6.7 | 13 | 4.1 | 58 | 155 | — | — |
| GW1843U89 | 11 | >1000 | 277 | >1000 | 5.8 | 32 | — | — |

Experiments were performed in standard RPMI1640/10% dialyzed fetal bovine serum. Growth inhibition results are presented as mean values IC50 values (nM) from 2-3 experiments. For GARFTase assays, results are shown as mean IC50s. SEM values are shown in parentheses.

Human Proton-Coupled Folate Transporter (hPCFT) Studies.

Figure 4:
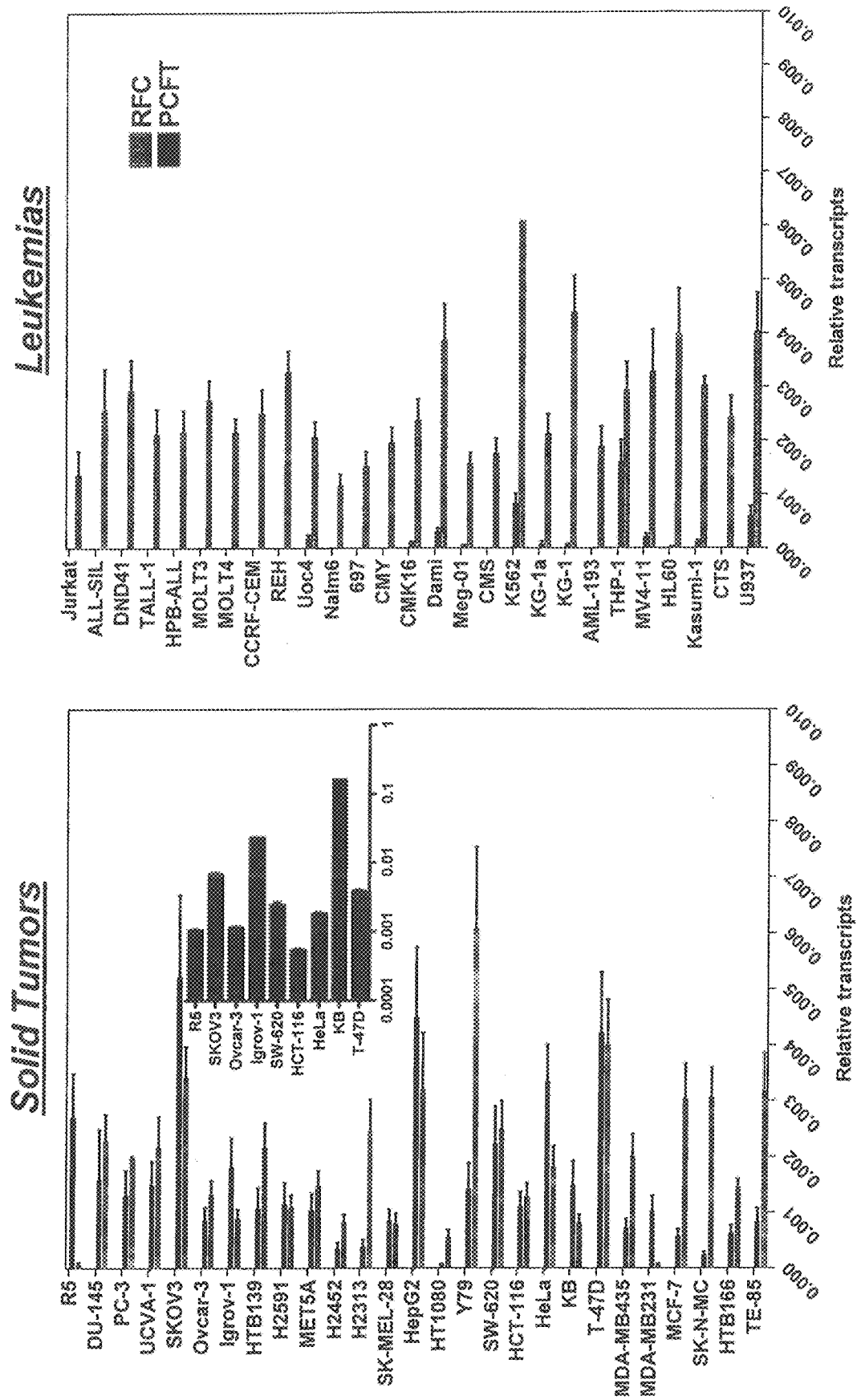
FIG. 4 shows hRFC and hPCFT transcript levels in a solid tumor and leukemia cell lines.

Following reports of a novel pH transporter termed PCFT in the proximal small intestine and possibly solid tumors, the inventors' established an expression profile of this transporter compared to hRFC and FRα in a wide range of cell lines derived from human solid tumors and leukemias. mRNA levels for hPCFT, hRFC and FRα were measured by real-time RT-PCR (qPCR) and normalized to levels of glyceraldyde-3-phosphate dehydrogenase. Results shown in FIG. 4 clearly demonstrate appreciable hPCFT transcripts in a large number of human solid tumor cell lines of different origins (e.g., breast, prostate, ovarian, etc.) and uniformly low level hPCFT in human leukemias. hPCFT levels were highest in SKOV3 (ovarian), HepG2 (hepatoma), HeLa (cervical), and T47D (breast) cancer cells. hRFC transcripts were detected in all cell lines with exception of HeLa R5 and MDA-MB-231 (both documented to express low to undetectable hRFC). FRα was only detected in a small subset of ovarian, cervical, and breast cell lines (inset). FIG. 4 sets forth hRFC and hPCFT transcript levels in solid tumor and leukemia cell lines. Transcripts levels were measured by qPCR from total RNAs using a Roche 480 Lightcycler and Sybr Green1 detection. hRFC/hPCFT transcript levels were normalized to GAPDH transcripts. The inset (black bars) shows results for solid tumors in which FR alpha transcripts could be detected. FR alpha could not be detected in the remaining solid tumors and all of the leukemia cells. The tumor types for the solid tumors shown in FIG. 4 are as follows: DU-145, PC-3 (prostate); UCVA-1 (pancreas); SKOV3, Ovcar-3, Igrov-1 (ovary); HTB139 (muscle); H2591, MET5A, H2452, H2313 (mesothelioma); SK-MEL-28 (melanoma); HepG2 (hepatoma); HT1080 (fibrosarcoma); Y79 (eye); SW-620, HCG-116 (colon); HeLa, R5, KB (cervical); T-47D, MDA-MB435, MDA-MB231, MCF-7 (breast); SK-N-MC (brain); and HTB166, TE-85 (bone).

Figure 5:
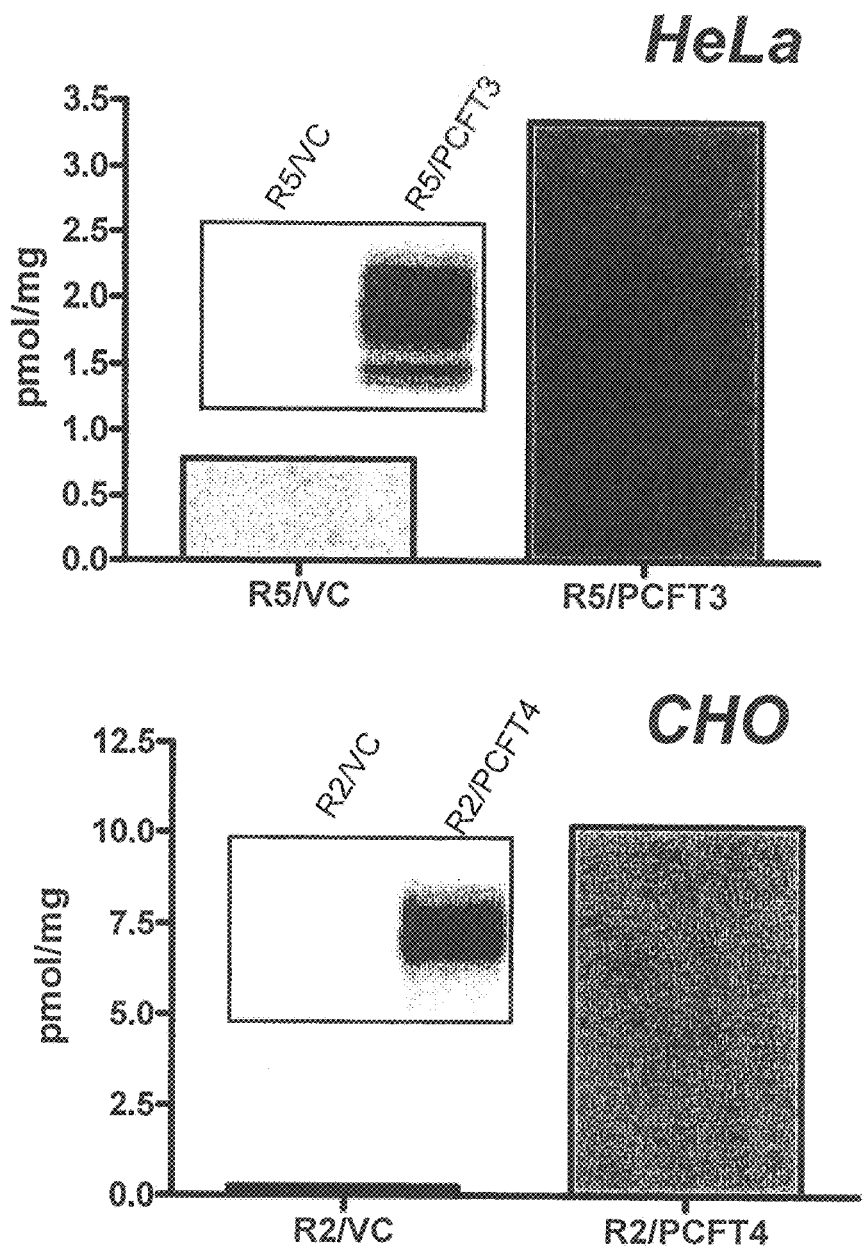
FIG. 5 shows transfection of HeLa R5 and CHO R2 cells with hPCFT$^{Myc\text{-}his6}$.

To study the functional and biochemical properties of hPCFT, the inventors prepared a myc-his6 tagged hPCFT (hPCFT$^{myc\text{-}his6}$) cDNA construct by RT-PCR from RNA prepared from wild type (wt) HeLa cells. hPCFT$^{myc\text{-}his6}$ (in pCDNA3.1 plasmid) was transiently expressed in R5 HeLa cells (expresses some low level of hPCFT), and assayed for hPCFT$^{Myc\text{-}his6}$ protein on westerns with Myc-specific antibody and transport activity at pH 5.5 for comparison with mock (vector control) transfected R5 cells (FIG. 5, upper panel). To generate stable transfectants, PCFT- and RFC-null R2 CHO cells were electroporated with the hPCFT$^{myc\text{-}his6}$-pCDNA3.1 construct. Cells were selected with G418 and screened for hPCFT$^{myc\text{-}his6}$ protein. The best clone (designated R2-hPCFT#4) was further characterized (FIG. 5, lower panel). A high level of hPCFT$^{Myc\text{-}His6}$ protein was detected on Western blots (westerns) accompanying significant [$^3$H]Mtx transport at pH 5.5. Transport was negligible at pH 7.2-7.4 (not shown). For hRFC-expressing pC43-10 cells, [$^3$H]MTX transport was active at pH 7.2-7.4 but was undetectable at pH 5.5 (data not shown). FIG. 5 shows transfection of HeLa R5 and CHO R2 Cells with hPCFT-Myc-his10. Cells were transfected with hPCFTMyc-his6 either transiently (HeLa) or stably (R2). PCFTMyc-His10 protein was measured on westerns with Myc specific antibody (insets) and hPCFT activity was measured in MES-buffered saline at pH 5.5 with 1 micromolar 3H-Mtx as substrate.

In growth inhibition assays, the inventors found that sensitivities to assorted classical antifolates including methotrexate (MTX), GW1843U89, lometrexol, pemetrexed, PT523, and raltitrexed for hPCFT$^{Myc\text{-}his6}$-expressing R2-hPCFT#4 cells and hRFC-expressing pC43-10 cells were all increased (~4 to 8-fold and ~10- to 150-fold, respectively), in comparison with vector control R2 cells (Tables 1 and 2). Thus, even at the relatively neutral pH (~7.2) of tissue culture media, classical antifolates appear to be substrates for hPCFT, as reflected in patterns of growth inhibition in the hPCFT-transfected and mock transfected CHO cells. By comparing results with R2-hPCFT#4 and pC43-10 cells, only the antifolate PT523 was completely selective in its effects toward hRFC over hPCFT, whereas none of these agents showed significant selectivity toward hPCFT over hRFC.

Figure 6:
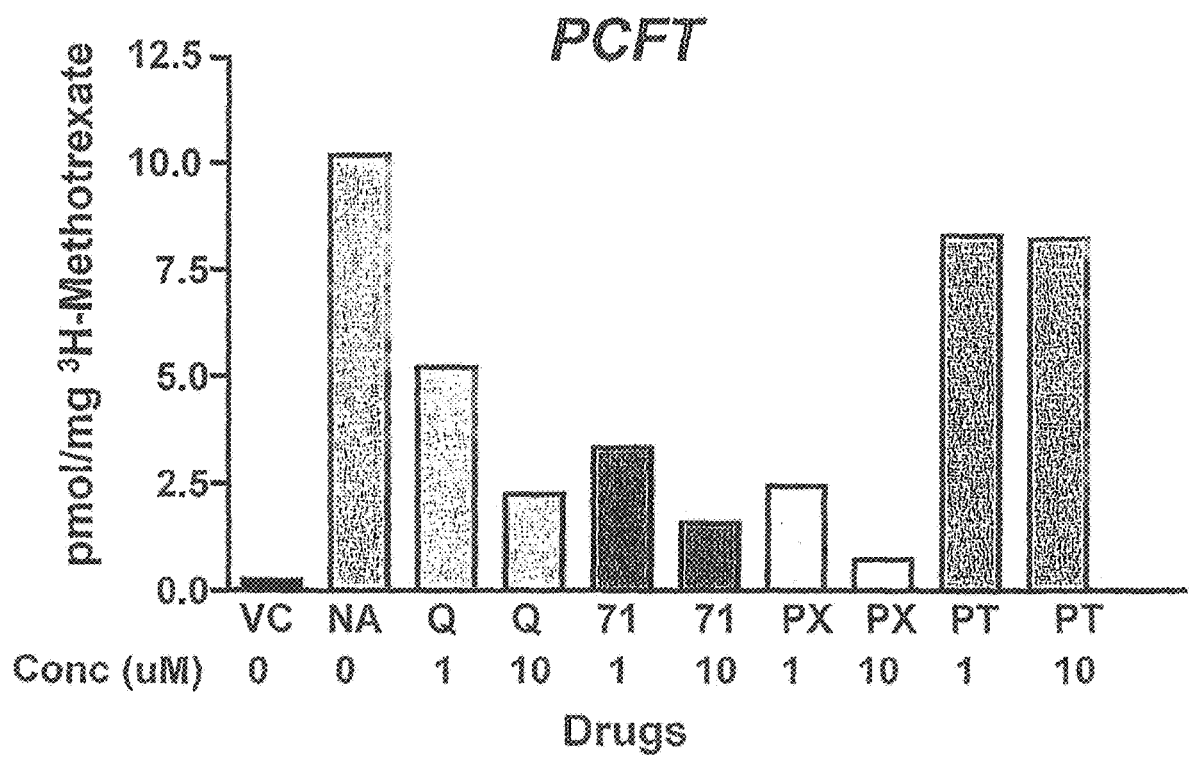
FIG. 6 shows transport inhibition of transiently transfected R5 HeLa cells with hPCFT$^{Myc\text{-}his6}$ and inhibition by Compounds AAG120366-2 (shown as "Q" in FIG. 6), AAG154353 (shown as "71" in FIG. 6), and PT523 (shown as "PT" in FIG. 6). Assays used $^3$H-methotrexate at 37° C. in pH 5.5 MES-buffered saline without additions (shown as "NA" in FIG. 6) or in the presence of 1 or 10 micromolar inhibitor Compounds "Q", "71", and "PT" as set forth in FIG. 6.

The compounds of Formula I of the present invention, for example, have structures with modifications in several regions, including but not limited to the pteridine moeity, the carbon bridge region of the side chain, the p-aminobenzoic acid, or terminal glutamate, and combinations thereof. For example, by standard growth inhibition assays, we identified a novel 6-substituted pyrrolo[2,3-d]pyrimidine antifolate, namely AAG154353, with striking sensitivity toward R2-hPCFT#4 cells (~20- to 30-fold greater than those for vector-control R2 cells) (Table 2) and a nearly complete lack of drug activity toward hRFC-expressing pC43-10 cells (Table 1). Specificity for hPCFT over hRFC was further suggested by assays of direct competition with [$^3$H]MTX for cellular uptake by R2-hPCFT#4 (FIG. 6). In both transport and cytotoxicity experiments, compound AAG154353 exhibited potencies similar to that for pemetrexed, the best substrate yet described for hPCFT. However, the hRFC substrate, PT523, was completely inert in inhibiting cell proliferation or [$^3$H]MTX uptake with R2-hPCFT#4 cells. In contrast to pemetrexed, compound AAG154353 showed negligible inhibition of [$^3$H]MTX transport from hRFC in pC43-10 cells (at pH 7.2-7.4) (not shown).

Identification of Intracellular Enzyme Target.

Compound AAG120366-2 was previously reported by this applicant to potently inhibit GARFTase, the first folate-dependent step in the de novo purine biosynthetic pathway (Deng et al., 2008). To localize the probable enzyme target(s) for compound AAG154353, we tested the growth inhibitory effects of this compounds toward KB in the presence of adenosine (60 µM) or thymidine (10 µM). Thymidine (10 µM) did not alter the growth inhibitory effects of AAG154353 whereas adenosine (60 µM) was completely protective, thus establishing the de novo purine biosynthetic pathway as the primary target. Compound AAG154353 was completely protected by 5-amino-4-imidazolecarboxamide (AICA) (320 µM) which identified GARFTase as the likely intracellular target. We used in vitro and in situ GARFTase inhibition assays with antifolate analogs to confirm inhibitions of this enzyme target. With the purified recombinant mouse GARFTase, compounds AAG154353 and AAG154360 were inhibitory with IC50s of 0.06 µM and 3.31 µM, respectively (Table 1). In the in situ GARFTase assay, incorporation of $^{14}$C-glycine into formyl glycinamide ribonucleotide was measured and was inhibited at nM concentrations of the drugs, with the most potent effects by inhibitor AAG154353 (Table 1). The dramatic differences in inhibition potencies by in situ versus in vitro assays of GARFTase for all these agents likely reflect an exacerbation of enzyme binding affinities by drug polyglutamates within cells.

TABLE 2

Growth inhibition by antifolate drugs toward hPCFT- and hRFC stable R2 CHO transfectants.

| Analogs | R2-hPCFT#4 | R2/VC |
|---|---|---|
| Methotrexate | 143.25 ± 29.4 | >1000 |
| GW1843U89 | 39.23 ± 7.31 | 135.76 ± 13.99 |
| Lometrexol | 183.28 ± 12.61 | >1000 |
| Pemetrexed | 27.51 ± 3.26 | 150.42 ± 22.54 |
| PT523 | >1000 | >1000 |
| Raltitrexed | 63.76 ± 3.26 | 604.39 ± 53.63 |
| AAG120366-2 | 29.14 ± 4.72 | 490.89 ± 77.58 |
| AAG154353 | 48.25 ± 17.75 | >1000 |

Experiments were performed in folate-free RPMI1640/10% dialyzed fetal bovine serum supplemented with 25 nM leucovorin. Growth inhibition was measured by a florescence (Cell TiterBlue)-based assay after 96 h of exposure to a range of inhibitor concentrations. Results are presented as 50% inhibitory concentrations. (IC$_{50}$'s)

Our results establish a high frequency of expression of hPCFT in solid tumors over leukemias. hRFT is expressed in both solid tumors and leukemias whereas FRα is expressed exclusively in a subset of solid tumors. Our results with compound AAG154353 are unprecedented in that they are the first to exhibit a unique and selective binding to FRα and hPCFT over hRFC that results in a potent growth inhibition even at physiologic pH. Given the acidic pH optimum for hPCFT (pH 5.5-6.8), these growth inhibitory effects are clearly exacerbated at lower pH values (6.5-6.8) as occurs, for example, in a solid tumor environment. Indeed, our initial studies over a range of pH values establish a 2-3-fold increased inhibition of hPCFT transport at acid (ph<7) over neutral (pH>7) conditions.

The development of novel small molecule cytotoxins such as the compounds of Formula I of the present invention that are selectively transported by hPCFT provide exciting new therapeutic applications for solid tumor targeting. This is based on the notion of effectively "highjacking" an essential biological characteristic of solid tumors, namely their acidic microenvironment, for selective delivery of the cytotoxic compounds of the present invention.

Synthesis of Compounds

Chemistry

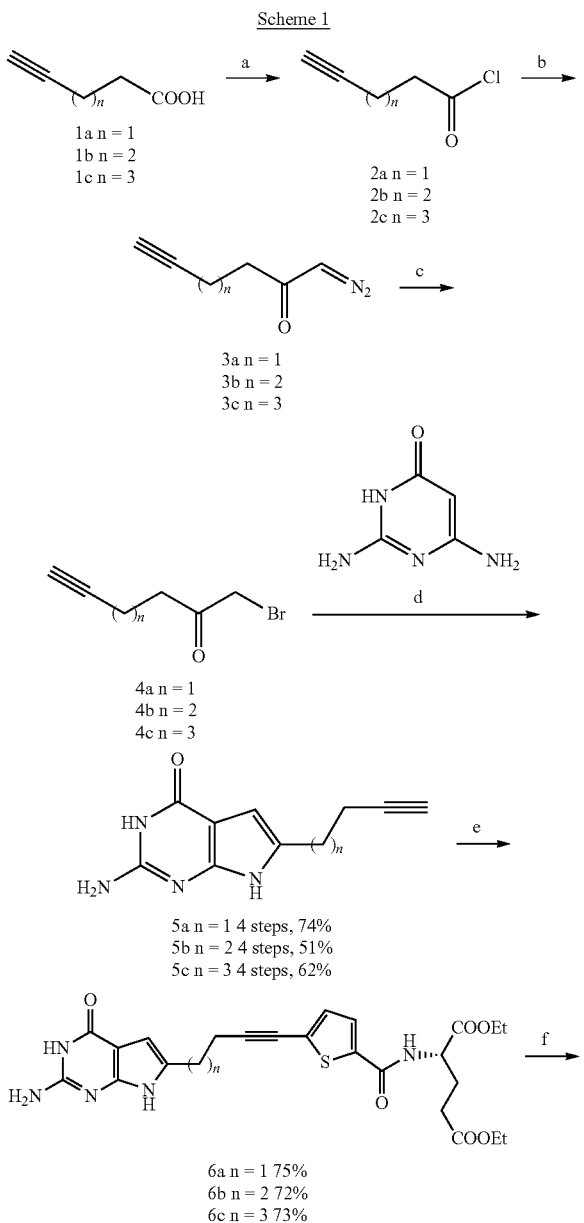

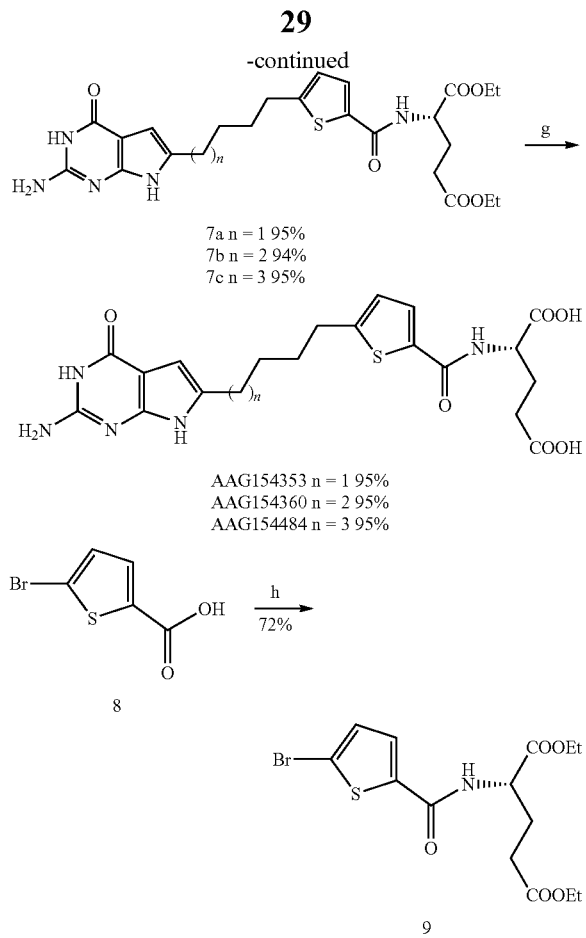

days afforded the 6-substituted pyrrolo[2,3-d]pyrimidines 5a-c (51-74% yield). Compounds 6a-c were obtained by a Sonogashira coupling of 5a-c with (S)-2-[(5-bromo-thiophene-2-carbonyl)-amino]-pentanedioic acid diethyl ester 9. Hydrogenation and saponification of 6a-c afforded AAG154353, AAG154360 and AAG154484, respectively. Compound 9 (Scheme 1) was synthesized by coupling the commercially available 5-bromo-2-thiophene-carboxylic acid 8 and L-glutamate diethyl ester hydrochloride in 72% yield.

a. oxalyl chloride, CH$_2$Cl$_2$, reflux, 1 h; b. diazomethane, Et$_2$O, r.t., 1 h; c. HBr, 70-80° C., 2 h; d. DMF, r.t., 3 d; e. 9, CuI, Pd(0)(PPh$_3$)$_4$, Et$_3$N, DMF, rt, 12 h; f. 5% Pd/C, H$_2$, 55 psi, 2 h; g. (i) 1N NaOH, r.t., 6 h; (ii) 1N HCl; h. N-methylmorpholine, 2-chloro-4,6-dimethoxy-1,3,5-triazine, L-glutamate diethyl ester hydrochloride, DMF, rt, 12 h.

Target compounds AAG154353, AAG154360 and AAG154484 were synthesized as shown in Scheme 1. Commercially available pent-4-ynoic acid 1a or hex-5-ynoic acid 1b or hept-6-ynoic acid 1c (Scheme 1) was converted to the acid chlorides 2a-c and immediately reacted with diazomethane followed by 48% HBr to give the desired α-bromomethylketones 4a-c. Condensation of 2,4-diamino-6-hydroxypyrimidine with 4a-c at room temperature for 3

Intermediates for compounds AAG154468 and AAG154479 were synthesized as shown in Scheme 2. Direct saponification of 6a and 6c afforded AAG154468 and AAG154479 in 95% yield.

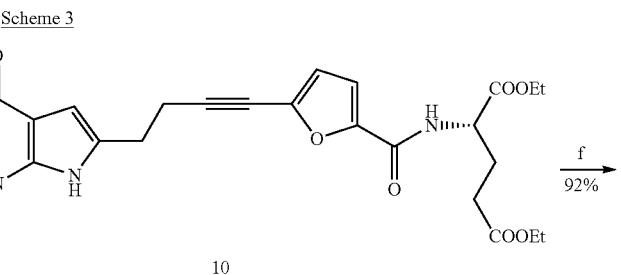

-continued

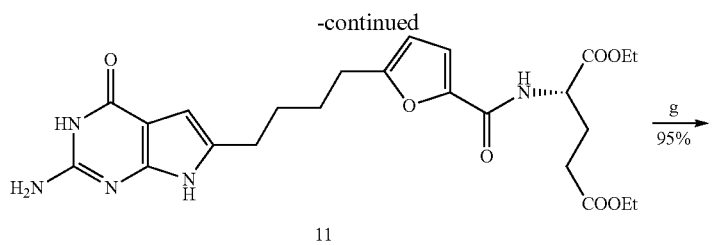

11

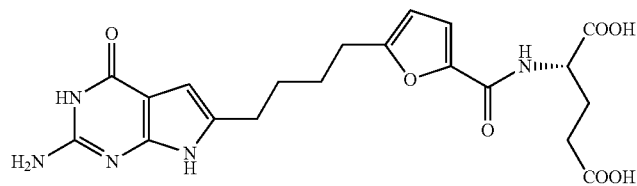

AAG154489

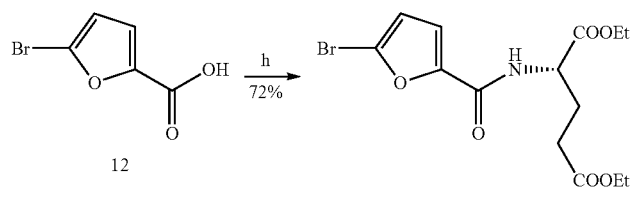

e. 13, CuI, Pd(0)(PPh₃)₄, Et₃N, DMF, rt, 12 h; f. 5% Pd/C, H₂, 55 psi, 2 h; g. (i) 1N NaOH, r.t., 6 h; (ii) 1N HCl; h. N-methylmorpholine, 2-chloro-4,6-dimethoxy-1,3,5-triazine, L-glutamate diethyl ester hydrochloride, DMF, rt, 12 h.

AAG154489 was synthesized as shown in Scheme 3. Compounds 10 was obtained by a Sonogashira coupling of 5a (from scheme 1) with (S)-2-[(5-bromo-furan-2-carbonyl)-amino]-pentanedioic acid diethyl ester 13. Compound 13 (Scheme 3) was synthesized by coupling the commercially available 5-bromo-2-furan-carboxylic acid 12 and L-glutamate diethyl ester hydrochloride in 72% yield. Hydrogenation and saponification of 10 afforded AAG154489.

Scheme 4

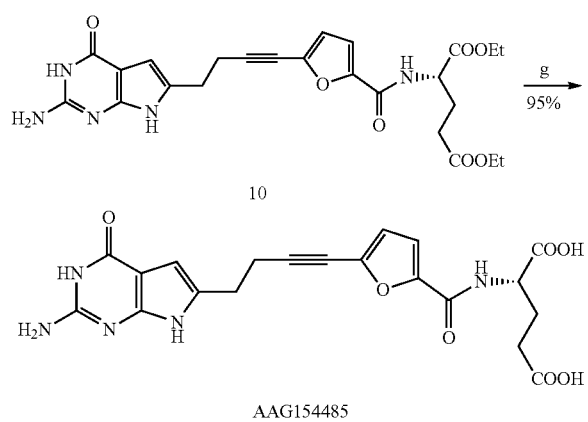

g. (i) 1N NaOH, r.t., 6 h; (ii) 1N HCl

AAG154485 was synthesized as shown in Scheme 4. Direct saponification of 10 afforded AAG154485 in 95% yield.

Experimental Section

All evaporations were carried out in vacuo with a rotary evaporator. Analytical samples were dried in a CHEM-DRY vacuum (0.2 mm Hg) drying oven over $P_2O_5$. Melting points were determined on a MELTEMP II melting point apparatus with FLUKE 51 K/J electronic thermometer and are uncorrected. NMR spectra for proton ($^1$H) were recorded on a Bruker WH-300 (300 MHz) spectrometer. The chemical shift values are expressed in ppm (parts per million) relative to tetramethylsilane as internal standard; s=singlet, d=doublet, t=triplet, q=quartet, m=multiplet, br=broad singlet. The relative integrals of peak areas agreed with those expected for the assigned structures. Thin-layer chromatography (TLC) was performed on PE SIL G/UV silica gel plates with fluorescent indicator, and the spots were visualized under 254 and 365 nm illumination. Proportions of solvents used for TLC are by volume. Column chromatography was performed on 230-400 mesh silica gel purchased from Fisher, Somerville, N.J. Elemental analyses were performed by Atlantic Microlab, Inc., Norcross, Ga. Element compositions are within ±0.4% of the calculated values. Fractional moles of water or organic solvents frequently found in some analytical samples of antifolates were not prevented despite 24-48 h of drying in vacuo and were confirmed where possible by their presence in the $^1$H NMR spectra. High resolution mass spectrometry (HRMS) was performed on a Waters Q-TOF (API-US) by Department of Chemistry, University of Pittsburgh, Pittsburgh, Pa. All solvents and chemicals were purchased from Aldrich Chemical Co. and Fisher Scientific and were used as received.

General Procedure for the Synthesis of Compounds 5a-c

To 1a-c (10 mmol) in a 250 mL flask were added oxalyl chloride (7.61 g, 60 mmol) and anhydrous $CH_2Cl_2$ (20 mL). The resulting solution was refluxed for 1 h and then cooled to room temperature. After evaporating the solvent under reduced pressure, the residue 2a-c were dissolved in 20 mL of Et₂O. The resulting solution was added drop wise to an ice-cooled diazomethane (generated in situ from 15 g diazald by using Aldrich Mini Diazald Apparatus) in an ice bath over 10 min. The resulting mixture was allowed to stand for 30 min and then stirred for an additional 1 h. To this solution was added 48% HBr (20 mL). The resulting mixture was refluxed for 1.5 h. After cooling to room temperature, the organic layer was separated and the aqueous layer extracted with Et₂O (200 mL×2). The combined organic layer and Et₂O extract was washed with two portions of 10% Na₂CO₃ solution and dried over Na₂SO₄. Evaporation of the solvent afforded 4a-c in 94% yield. To a suspension of 2,6-diaminopyrimidin-4-one (1.26 g, 10 mmol) in anhydrous DMF (25 mL) was added 4a-c (about 9.4 mmol). The resulting mixture was stirred under N₂ at room temperature for 3 days. After evaporation of solvent under reduced pressure, MeOH (20 mL) was added followed by silica gel (5 g). The resulting plug was loaded on to a silica gel column (3.5×12 cm) and eluted with CHCl₃ followed by 3% MeOH in CHCl₃ and then 5% MeOH in CHCl₃. Fractions with an $R_f$=0.58 (TLC) were pooled and evaporated to afford 5a-c as white powder.

2-amino-6-but-3-ynyl-3,7-dihydro-pyrrolo[2,3-d]pyrimidin-4-one (5a)

Compound 5a was prepared using the general method described for the preparation of 5a-c, from pent-4-ynoic acid 1a (0.98 g, 10 mmol) to give 1.4 g (74%) of 5a as white powder. mp 230-231° C.; ¹H NMR (DMSO-d₆): δ 2.41-2.45 (m, 2H), 2.64-2.67 (m, 2H), 2.77 (t, J=2 Hz, 1H), 5.93 (s, 1H), 5.98 (s, 2H), 10.13 (s, 1H), 10.81 (s, 1H). HRMS calcd for C₁₀H₁₀N₄O (M⁺), 203.0933; found: 203.0925.

2-amino-6-pent-4-ynyl-3,7-dihydro-pyrrolo[2,3-d]pyrimidin-4-one (5b)

Compound 5b was prepared using the general method described for the preparation of 5a-c, from hex-5-ynoic acid 1b (1.12 g, 10 mmol) to give 1.1 g (51%) of 5b as white powder. mp 233-234° C.; ¹H NMR (DMSO-d₆): δ 1.64-1.79 (m, 2H), 2.14-2.20 (m, 2H), 2.58-2.61 (t, J=10 Hz, 2H), 2.80-2.82 (t, J=3.2 Hz, 1H), 5.95 (s, 1H), 6.53 (s, 2H), 10.70 (s, 1H), 11.14 (s, 1H).

2-amino-6-hex-5-ynyl-3,7-dihydro-pyrrolo[2,3-d]pyrimidin-4-one (5c)

Compound 5c was prepared using the general method described for the preparation of 5a-c, from hept-6-ynoic acid 1c (1.26 g, 10 mmol) to give 1.43 g (62%) of 5c as white powder. mp 236-237° C.; ¹H NMR (DMSO-d₆): δ 1.40-1.47 (m, 2H), 1.52-1.67 (m, 2H), 2.13-2.17 (m, 2H), 2.46 (m, 2H), 2.75-2.77 (m, 1H), 5.87 (s, 1H), 6.16 (s, 2H), 10.31 (s, 1H), 10.90 (s, 1H).

General Procedure for the Synthesis of Compounds 6a-c

To a 250-mL round-bottomed flask, equipped with a magnetic stirrer and gas inlet, were added a mixture of tetrakis (triphenylphosphine)palladium(0) (185 mg, 0.16 mmol), triethylamine (1.01 g, 10 mmol), (S)-2-[(5-bromothiophene-2-carbonyl)-amino]-pentanedioic acid diethyl ester 9 (588 mg, 1.5 mmol) and anhydrous DMF (20 mL). To the stirred mixture, under N₂, was added copper(I) iodide (30 mg, 0.16 mmol) and 5a-c (1 mmol), and the reaction mixture was stirred at room temperature overnight (17-18 h). After evaporation of solvent under reduced pressure, MeOH (20 mL) was added followed by silica gel (5 g). The resulting plug was loaded on to a silica gel column (3.5×12 cm) and eluted with CHCl₃ followed by 3% MeOH in CHCl₃ and then 5% MeOH in CHCl₃. Fractions with an $R_f$=0.53 (TLC) were pooled and evaporated to afford 6a-c as brown powder.

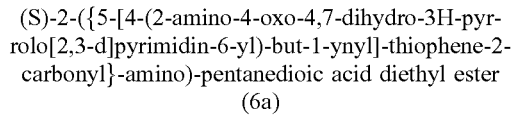
(S)-2-({5-[4-(2-amino-4-oxo-4,7-dihydro-3H-pyrrolo[2,3-d]pyrimidin-6-yl)-but-1-ynyl]-thiophene-2-carbonyl}-amino)-pentanedioic acid diethyl ester (6a)

Compound 6a was prepared using the general method described for the preparation of 6a-c, from 5a (202 mg, 1 mmol) to give 386 mg (75%) of 6a as brown powder. mp 81-82° C.; ¹H NMR (DMSO-d₆): δ 1.16-1.21 (m, 6H), 1.93-2.15 (m, 2H), 2.40-2.45 (t, J=10 Hz, 2H), 3.06-3.15 (m, 4H), 4.01-4.15 (m, 4H), 4.35-4.43 (m, 1H), 6.00 (s, 1H), 6.04 (s, 2H), 7.22-7.23 (d, J=5.2 Hz, 1H), 7.77-7.78 (d, J=5.2 Hz, 1H), 8.83-8.85 (d, J=10 Hz, 1H), 10.18 (s, 1H), 10.89 (s, 1H). HRMS calcd for C₂₄H₂₇N₅O₆S (M⁺), 514.1760; found: 514.1753.

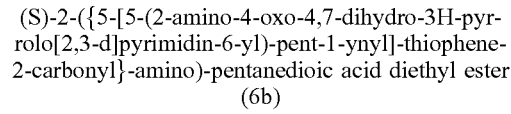
(S)-2-({5-[5-(2-amino-4-oxo-4,7-dihydro-3H-pyrrolo[2,3-d]pyrimidin-6-yl)-pent-1-ynyl]-thiophene-2-carbonyl}-amino)-pentanedioic acid diethyl ester (6b)

Compound 6b was prepared using the general method described for the preparation of 6a-c, from 5b (216 mg, 1 mmol) to give 380 mg (72%) of 6b as brown powder. mp 84-85° C.; ¹H NMR (DMSO-d₆): δ 1.16-1.20 (m, 6H), 1.81-1.90 (m, 2H), 1.92-2.13 (m, 2H), 2.40-2.45 (t, J=10 Hz, 2H), 2.46 (m, 2H), 2.59-2.64 (t, J=9.6 Hz, 2H), 4.00-4.14 (m, 4H), 4.35-4.43 (m, 1H), 5.91 (s, 1H), 5.99 (s, 2H), 7.24-7.25 (d, J=5.2 Hz, 1H), 7.77-7.78 (d, J=5.2 Hz, 1H), 8.82-8.84 (d, J=10 Hz, 1H), 10.14 (s, 1H), 10.86 (s, 1H).

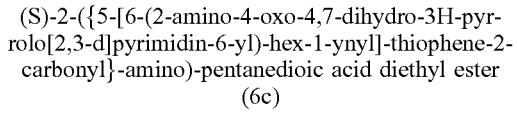
(S)-2-({5-[6-(2-amino-4-oxo-4,7-dihydro-3H-pyrrolo[2,3-d]pyrimidin-6-yl)-hex-1-ynyl]-thiophene-2-carbonyl}-amino)-pentanedioic acid diethyl ester (6c)

Compound 6c was prepared using the general method described for the preparation of 6a-c, from 5c (230 mg, 1 mmol) to give 396 mg (73%) of 6c as brown powder. mp 85-86° C.; ¹H NMR (DMSO-d₆): δ 1.13-1.19 (m, 6H), 1.48-1.57 (m, 2H), 1.62-1.71 (m, 2H), 1.91-2.12 (m, 2H), 2.39-2.43 (t, J=7.6 Hz, 2H), 2.46-2.48 (m, 4H), 4.00-4.12 (m, 4H), 4.34-4.40 (m, 1H), 5.87 (s, 1H), 5.96 (s, 2H), 7.23-7.24 (d, J=3.6 Hz, 1H), 7.75-7.76 (d, J=3.6 Hz, 1H), 8.80-8.82 (d, J=7.6 Hz, 1H), 10.12 (s, 1H), 10.81 (s, 1H).

General Procedure for the Synthesis of Compounds 7a-c

To a Parr flask were added 6a-c (0.75 mmol), 10% palladium on activated carbon (120 mg), and MeOH (100 mL). Hydrogenation was carried out at 55 psi of H₂ for 4 h. The reaction mixture was filtered through Celite, washed with MeOH (100 mL) and concentrated under reduced pressure to give 7a-c as yellow powder.

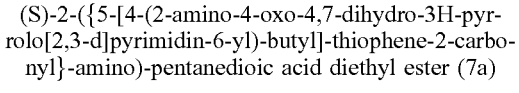
(S)-2-({5-[4-(2-amino-4-oxo-4,7-dihydro-3H-pyrrolo[2,3-d]pyrimidin-6-yl)-butyl]-thiophene-2-carbonyl}-amino)-pentanedioic acid diethyl ester (7a)

Compound 7a was prepared using the general method described for the preparation of 7a-c, from 6a (386 mg, 0.75 mmol) to give 369 mg (95%) of 7a as yellow powder. mp 74-75° C.; ¹H NMR (DMSO-d₆): δ 1.13-1.20 (m, 6H), 1.62

(m, 4H), 1.89-2.13 (m, 2H), 2.39-2.44 (t, J=10 Hz, 2H), 2.69 (m, 2H), 2.81 (m, 2H), 4.00-4.13 (m, 4H), 4.34-4.42 (m, 1H), 5.85 (s, 1H), 5.97 (s, 2H), 6.88-6.89 (d, J=4.8 Hz, 1H), 7.67-7.68 (d, J=4.8 Hz, 1H), 8.60-8.63 (d, J=10 Hz, 1H), 10.13 (s, 1H), 10.81 (s, 1H). HRMS calcd for $C_{24}H_{31}N_5O_6S$ (M$^+$), 518.2073; found: 518.2077.

(S)-2-({5-[5-(2-amino-4-oxo-4,7-dihydro-3H-pyrrolo[2,3-d]pyrimidin-6-yl)-pentyl]-thiophene-2-carbonyl}-amino)-pentanedioic acid diethyl ester (7b)

Compound 7b was prepared using the general method described for the preparation of 7a-c, from 6b (380 mg, 0.72 mmol) to give 360 mg (94%) of 7b as yellow powder. mp 77-78° C.; $^1$H NMR (DMSO-d$_6$): δ 1.12-1.21 (m, 8H), 1.53-1.67 (m, 4H), 1.91-2.14 (m, 2H), 2.39-2.43 (t, J=10 Hz, 2H), 2.46 (m, 2H), 2.77-2.82 (t, J=9.6 Hz, 2H), 4.00-4.14 (m, 4H), 4.33-4.41 (m, 1H), 5.84 (s, 1H), 5.97 (s, 2H), 6.88-6.89 (d, J=4.8 Hz, 1H), 7.68-7.69 (d, J=4.8 Hz, 1H), 8.60-8.63 (d, J=10 Hz, 1H), 10.12 (s, 1H), 10.79 (s, 1H).

(S)-2-({5-[6-(2-amino-4-oxo-4,7-dihydro-3H-pyrrolo[2,3-d]pyrimidin-6-yl)-hexyl]-thiophene-2-carbonyl}-amino)-pentanedioic acid diethyl ester (7c)

Compound 7c was prepared using the general method described for the preparation of 7a-c, from 6c (396 mg, 0.73 mmol) to give 379 mg (94%) of 7c as yellow powder. mp 78-79° C.; $^1$H NMR (DMSO-d$_6$): δ 1.15-1.19 (m, 6H), 1.23-1.31 (m, 4H), 1.47-1.68 (m, 4H), 1.90-2.14 (m, 2H), 2.37-2.48 (m, 6H), 4.02-4.12 (m, 4H), 4.33-4.41 (m, 1H), 5.84 (s, 1H), 5.96 (s, 2H), 7.08-7.09 (d, J=3.6 Hz, 1H), 7.78-7.79 (d, J=3.6 Hz, 1H), 8.72-8.74 (d, J=7.6 Hz, 1H), 10.11 (s, 1H), 10.79 (s, 1H).

General Procedure for the Synthesis of Target Compounds AAG154353, AAG154360, AAG154484, AAG154468, AAG154479, AAG154489 and AAG154485

To a solution of 7a-c (0.7 mmol) in MeOH (10 mL) was added 1 N NaOH (10 mL) and the mixture was stirred under N$_2$ at room temperature for 16 h. TLC showed the disappearance of the starting material (R$_f$=0.45) and one major spot at the origin (MeOH/CHCl$_3$ 1:5). The reaction mixture was evaporated to dryness under reduced pressure. The residue was dissolved in water (10 mL), the resulting solution was cooled in an ice bath, and the pH was adjusted to 3-4 with drop wise addition of 1 N HCl. The resulting suspension was frozen in a dry ice-acetone bath, thawed to 4-5° C. in the refrigerator, and filtered. The residue was washed with a small amount of cold water and dried in vacuum using P$_2$O$_5$ to afford the target compounds as white powder.

(S)-2-({5-[4-(2-amino-4-oxo-4,7-dihydro-3H-pyrrolo[2,3-d]pyrimidin-6-yl)-butyl]-thiophene-2-carbonyl}-amino)-pentanedioic acid (AAG154353)

Compound AAG154353 was prepared using the general method described for the preparation of target compounds, from 7a (369 mg, 0.71 mmol) to give 312 mg (95%) of AAG154353 as white powder. mp 179-180° C.; $^1$H NMR (DMSO-d$_6$): δ 1.62 (m, 4H), 1.91-2.05 (m, 2H), 2.31-2.36 (t, J=7.4 Hz, 2H), 2.69 (m, 2H), 2.81 (m, 2H), 4.29-4.43 (m, 1H), 5.87 (s, 1H), 6.10 (s, 2H), 6.87-6.88 (d, J=4 Hz, 1H), 7.67-7.68 (d, J=4 Hz, 1H), 8.49-8.52 (d, J=8 Hz, 1H), 10.26 (s, 1H), 10.88 (s, 1H), 12.42 (br, 2H). HRMS calcd for $C_{20}H_{23}N_5O_6S$ (M$^+$), 462.1447; found: 462.1462.

(S)-2-({5-[5-(2-amino-4-oxo-4,7-dihydro-3H-pyrrolo[2,3-d]pyrimidin-6-yl)-pentyl]-thiophene-2-carbonyl}-amino)-pentanedioic acid (AAG154360)

Compound AAG154360 was prepared using the general method described for the preparation of target compounds, from 7b (360 mg, 0.68 mmol) to give 306 mg (95%) of AAG154360 as white powder. mp 181-182° C.; $^1$H NMR (DMSO-d$_6$): δ 1.28-1.34 (m, 2H), 1.54-1.66 (m, 4H), 1.85-2.10 (m, 2H), 2.30-2.34 (t, J=7.4 Hz, 2H), 2.43-2.47 (t, J=7.6 Hz, 2H), 2.76-2.80 (t, J=7.6 Hz, 2H), 4.29-4.43 (m, 1H), 5.83 (s, 1H), 5.95 (s, 2H), 6.86-6.87 (d, J=4 Hz, 1H), 7.66-7.67 (d, J=4 Hz, 1H), 8.49-8.51 (d, J=8 Hz, 1H), 10.11 (s, 1H), 10.78 (s, 1H), 12.32 (br, 2H). HRMS calcd for $C_{21}H_{25}N_5O_6S$ (M$^+$), 476.1604; found: 476.1617.

(S)-2-({5-[6-(2-amino-4-oxo-4,7-dihydro-3H-pyrrolo[2,3-d]pyrimidin-6-yl)-hexyl]-thiophene-2-carbonyl}-amino)-pentanedioic acid (AAG154484)

Compound AAG154484 was prepared using the general method described for the preparation of target compounds, from 7c (379 mg, 0.69 mmol) to give 322 mg (95%) of AAG154484 as white powder. mp 183-184° C.; $^1$H NMR (DMSO-d$_6$): δ 1.27-1.35 (m, 2H), 1.44-1.67 (m, 6H), 1.87-2.10 (m, 2H), 2.31-2.35 (t, J=7.4 Hz, 2H), 2.37-2.44 (m, 4H), 4.30-4.38 (m, 1H), 5.84 (s, 1H), 5.95 (s, 2H), 7.07-7.08 (d, J=4 Hz, 1H), 7.77-7.78 (d, J=4 Hz, 1H), 8.60-8.62 (d, J=8 Hz, 1H), 10.12 (s, 1H), 10.79 (s, 1H), 12.46 (br, 2H). Anal. ($C_{22}H_{27}N_5O_6S$) C, H, N, S. calcd for $C_{22}H_{27}N_5O_6S.1H_2O$; C, 52.06; H, 5.64; N, 16.69; S, 6.32. Found: C, 52.39; H, 5.24; N, 13.30; S, 5.98.

(S)-2-({5-[4-(2-amino-4-oxo-4,7-dihydro-3H-pyrrolo[2,3-d]pyrimidin-6-yl)-but-1-ynyl]-thiophene-2-carbonyl}-amino)-pentanedioic acid (AAG154468)

Compound AAG154484 was prepared using the general method described for the preparation of target compounds, from 6a (50 mg, 0.1 mmol) to give 42 mg (95%) of AAG154468 as white powder. mp 196-197° C.; $^1$H NMR (DMSO-d$_6$): δ 1.85-2.11 (m, 2H), 2.31-2.36 (t, J=7.4 Hz, 2H), 2.76 (m, 4H), 4.30-4.38 (m, 1H), 5.92 (s, 1H), 5.99 (s, 2H), 7.20-7.21 (d, J=4 Hz, 1H), 7.74-7.75 (d, J=4 Hz, 1H), 8.69-8.71 (d, J=8 Hz, 1H), 10.15 (s, 1H), 10.86 (s, 1H), 12.47 (br, 2H). HRMS calcd for $C_{20}H_{19}N_5O_6S$ (M$^+$), 458.1134; found: 458.1155.

(S)-2-({5-[6-(2-amino-4-oxo-4,7-dihydro-3H-pyrrolo[2,3-d]pyrimidin-6-yl)-hex-1-ynyl]-thiophene-2-carbonyl}-amino)-pentanedioic acid (AAG154479)

Compound AAG154479 was prepared using the general method described for the preparation of target compounds, from 6c (50 mg, 0.09 mmol) to give 43 mg (95%) of AAG154479 as white powder. mp 197-198° C.; $^1$H NMR (DMSO-d$_6$): δ 1.44-1.67 (m, 4H), 1.87-2.10 (m, 2H), 2.23-2.45 (m, 4H), 4.30-4.38 (m, 1H), 5.87 (s, 1H), 5.95 (s, 2H), 7.21-7.22 (d, J=4 Hz, 1H), 7.73-7.74 (d, J=4 Hz, 1H), 8.66-8.68 (d, J=8 Hz, 1H), 10.12 (s, 1H), 10.81 (s, 1H), 12.58 (br, 2H). HRMS calcd for $C_{22}H_{23}N_5O_6S$ (M$^+$), 486.1447; found: 486.1452.

(S)-2-({5-[4-(2-amino-4-oxo-4,7-dihydro-3H-pyrrolo[2,3-d]pyrimidin-6-yl)-but-1-ynyl]-furan-2-carbonyl}-amino)-pentanedioic acid diethyl ester (10)

Compound 10 was prepared using the general method described for the preparation of 6a-c, from 5a (202 mg, 1 mmol) to give 249 mg (50%) of 10 as brown powder. mp 78-79° C.; $^1$H NMR (DMSO-d$_6$): δ 1.14-1.18 (m, 6H), 1.92-2.14 (m, 2H), 2.35-2.39 (t, J=7.6 Hz, 2H), 2.77-2.80 (m, 4H), 3.99-4.11 (m, 4H), 4.35-4.42 (m, 1H), 5.99 (s, 1H), 6.00 (s, 2H), 6.78-6.79 (d, J=3.6 Hz, 1H), 7.14-7.15 (d, J=3.6 Hz, 1H), 8.71-8.73 (d, J=7.6 Hz, 1H), 10.15 (s, 1H), 10.88 (s, 1H).

(S)-2-({5-[4-(2-amino-4-oxo-4,7-dihydro-3H-pyrrolo[2,3-d]pyrimidin-6-yl)-butyl]-furan-2-carbonyl}-amino)-pentanedioic acid diethyl ester (11)

Compound 11 was prepared using the general method described for the preparation of 7a-c, from 10 (249 mg, 0.5 mmol) to give 231 mg (92%) of 11 as yellow powder. mp 71-72° C.; $^1$H NMR (DMSO-d$_6$): δ 1.14-1.18 (m, 6H), 1.60-1.65 (m, 4H), 1.94-2.10 (m, 2H), 2.36-2.39 (t, J=7.2 Hz, 2H), 2.65-2.68 (m, 4H), 4.00-4.11 (m, 4H), 4.34-4.40 (m, 1H), 5.85 (s, 1H), 5.95 (s, 2H), 6.25-6.26 (d, J=3.6 Hz, 1H), 7.05-7.06 (d, J=3.6 Hz, 1H), 8.43-8.45 (d, J=7.6 Hz, 1H), 10.10 (s, 1H), 10.80 (s, 1H).

(S)-2-({5-[4-(2-amino-4-oxo-4,7-dihydro-3H-pyrrolo[2,3-d]pyrimidin-6-yl)-butyl]-furan-2-carbonyl}-amino)-pentanedioic acid (AAG154489)

Compound AAG154489 was prepared using the general method described for the preparation of target compounds, from 11 (231 mg, 0.46 mmol) to give 194 mg (95%) of AAG154489 as white powder. mp 174-175° C.; $^1$H NMR (DMSO-d$_6$): δ 1.62 (m, 4H), 1.87-2.10 (m, 2H), 2.28-2.32 (t, J=8 Hz, 2H), 2.65-2.68 (m, 4H), 4.29-4.43 (m, 1H), 5.86 (s, 1H), 5.95 (s, 2H), 6.25-6.26 (d, J=3.6 Hz, 1H), 7.04-7.05 (d, J=3.6 Hz, 1H), 8.29-8.31 (d, J=8 Hz, 1H), 10.12 (s, 1H), 10.80 (s, 1H), 12.47 (br, 2H). Anal. (C$_{20}$H$_{23}$N$_5$O$_7$) C, H, N. calcd for C$_{20}$H$_{23}$N$_5$O$_7$.1.25H$_2$O; C, 51.33; H, 5.49; N, 14.62. Found: C, 51.34; H, 5.36; N, 14.62.

(S)-2-({5-[4-(2-amino-4-oxo-4,7-dihydro-3H-pyrrolo[2,3-d]pyrimidin-6-yl)-but-1-ynyl]-furan-2-carbonyl}-amino)-pentanedioic acid (AAG154485)

Compound AAG154485 was prepared using the general method described for the preparation of target compounds, from 10 (50 mg, 0.1 mmol) to give 42 mg (95%) of AAG154485 as white powder. mp 193-194° C.; $^1$H NMR (DMSO-d$_6$): δ 1.88-2.11 (m, 2H), 2.28-2.32 (t, J=8 Hz, 2H), 2.78-2.80 (m, 4H), 4.30-4.38 (m, 1H), 5.98 (s, 1H), 5.99 (s, 2H), 6.78-6.79 (d, J=3.6 Hz, 1H), 7.14-7.15 (d, J=3.6 Hz, 1H), 8.57-8.59 (d, J=8 Hz, 1H), 10.16 (s, 1H), 10.88 (s, 1H), 12.45 (br, 2H). HRMS calcd for C$_{20}$H$_{19}$N$_5$O$_7$ (M$^+$), 441.1284; found: 441.1286.

General Procedure for the Synthesis of Compound 9 and 13

To a solution of 8 or 12 (10 mmol) in anhydrous DMF (20 mL) was added N-methylmorpholine (1.3 mL, 18 mmol) and 2-chloro-4,6-dimethoxy-1,3,5-triazine (2.16 g, 18 mmol). The resulting mixture was stirred at room temperature for 2 h. To this mixture was added N-methylmorpholine (1.3 mL, 18 mmol) and L-glutamate diethyl ester hydrochloride (3.6 g, 15 mmol). The reaction mixture was stirred for an additional 4 h at room temperature and then evaporated to dryness under reduced pressure. The residue was dissolved in the minimum amount of CH$_3$Cl/MeOH (4:1) and chromatographed on a silica gel column (2×15 cm) and with 5% EtOAc in hexane as the eluent. Fractions that showed the desired spot (TLC) were pooled and the solvent evaporated to dryness to afford 9 and 13 in 72% yield.

(S)-2-[(5-bromo-thiophene-2-carbonyl)-amino]-pentanedioic acid diethyl ester (9)

Compound 9 was prepared using the general method described for the preparation of compound 9 and 13, from 8 (2.07 g, 10 mmol) to give 2.82 g (72%) of 9 as yellow oil. $^1$H NMR (DMSO-d$_6$): δ 1.14-1.19 (m, 6H), 1.91-2.12 (m, 2H), 2.39-2.42 (t, J=5.6 Hz, 2H), 4.01-4.12 (m, 4H), 4.35-4.39 (m, 1H), 7.30-7.31 (d, J=3.2 Hz, 1H), 7.69-7.70 (d, J=3.2 Hz, 1H), 8.81-8.82 (d, J=6 Hz, 1H).

(S)-2-[(5-bromo-furan-2-carbonyl)-amino]-pentanedioic acid diethyl ester (13)

Compound 13 was prepared using the general method described for the preparation of compound 9 and 13, from 12 (1.91 g, 10 mmol) to give 2.71 g (72%) of 13 as yellow oil. $^1$H NMR (DMSO-d$_6$): δ 1.13-1.19 (m, 6H), 1.88-2.11 (m, 2H), 2.37-2.41 (t, J=7.2 Hz, 2H), 4.00-4.12 (m, 4H), 4.36-4.41 (m, 1H), 6.77-6.78 (d, J=3.6 Hz, 1H), 7.20-7.21 (d, J=3.6 Hz, 1H), 8.72-8.74 (d, J=7.6 Hz, 1H).

Synthesis and Experimental for Compound AAG154544

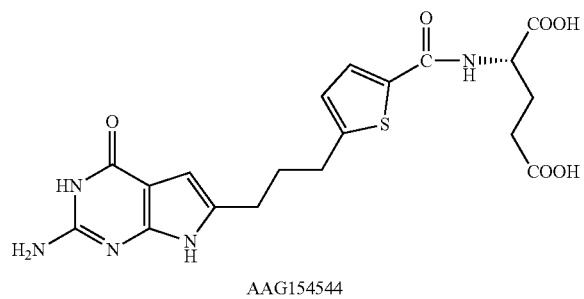 [SMILES: Nc1nc2[nH]c(CCCc3ccc(C(=O)N[C@@H](CCC(=O)O)C(=O)O)s3)cc2c(=O)[nH]1]

AAG154544

Chemistry

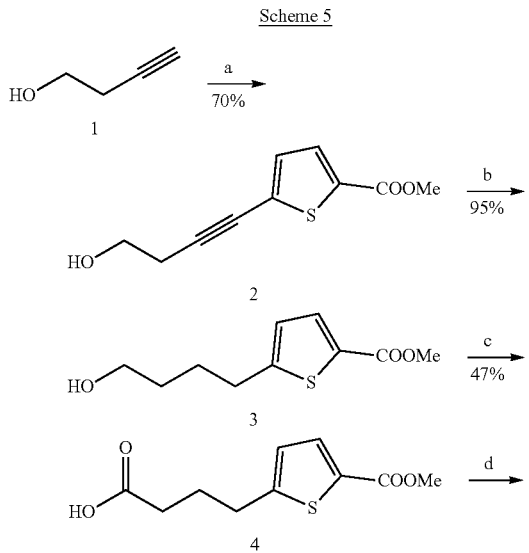

Scheme 5

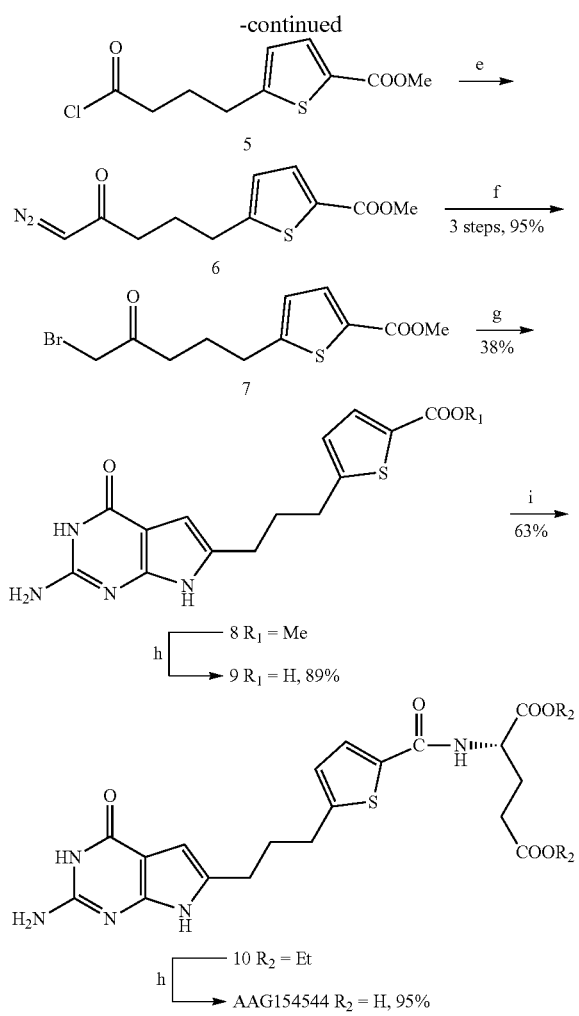

a. 5-Bromo-thiophene-2-carboxylic acid methyl ester, CuI, PdCl$_2$, PPh$_3$, Et$_3$N, CH$_3$CN, microwave, 100° C., 10 min; b. 10% Pd/C, H$_2$, 55 psi, MeOH, 2 h; c. H$_2$SO$_4$, CrO$_3$, 0° C.~r.t.; d. oxalyl chloride, CH$_2$Cl$_2$, reflux, 1 h; e. diazomethane, Et$_2$O, r.t., 1 h; f. HBr, 70-80° C., 2 h; g. 2,4-diamino-6-hydroxypyrimidine, DMF, r.t., 3 d; h. (i) 1N NaOH, r.t., 12 h; (ii) 1N HCl; i. N-methylmorpholine, 2-chloro-4,6-dimethoxy-1,3,5-triazine, L-glutamate diethyl ester hydrochloride, DMF, r.t., 12 h. Target compound AAG154544 was synthesized as shown in Scheme 5. Palladium-catalyzed Sonogashira coupling of 5-bromo-thiophene-2-carboxylic acid methyl ester with but-3-yn-1-ol 1 (Scheme 1) afforded thiophenebutynyl alcohol 2 (70%), which was catalytically hydrogenated to give the saturated alcohol 3 in quantitative yield. Subsequent oxidation of 3 using Jones' reagent afforded the carboxylic acid 4 (47%), which was converted to the acid chloride 5 and immediately reacted with diazomethane followed by 48% HBr to give the desired α-bromomethylketone 7. Condensation of 2,4-diamino-6-hydroxypyrimidine with 7 at room temperature for 3 days afforded the 6-substituted pyrrolo[2,3-d]pyrimidines 8 (38%). Hydrolysis of 8 afforded the corresponding free acid 9 (89%). Subsequent coupling with L-glutamate diethyl ester using 2-chloro-4,6-dimethoxy-1,3,5-triazine as the activating agent afforded the diesters 10. Final saponification of the diesters gave the desired compound AAG154544.

Experimental Section

All evaporations were carried out in vacuo with a rotary evaporator. Analytical samples were dried in a CHEM-DRY vacuum (0.2 mm Hg) drying oven over P$_2$O$_5$. Melting points were determined on a MELTEMP II melting point apparatus with FLUKE 51 K/J electronic thermometer and are uncorrected. NMR spectra for proton ($^1$H) were recorded on a Bruker WH-300 (300 MHz) spectrometer. The chemical shift values are expressed in ppm (parts per million) relative to tetramethylsilane as internal standard; s=singlet, d=doublet, t=triplet, q=quartet, m=multiplet, br=broad singlet. The relative integrals of peak areas agreed with those expected for the assigned structures. Thin-layer chromatography (TLC) was performed on PE SIL G/UV silica gel plates with fluorescent indicator, and the spots were visualized under 254 and 365 nm illumination. Proportions of solvents used for TLC are by volume. Column chromatography was performed on 230-400 mesh silica gel purchased from Fisher, Somerville, N.J. Elemental analyses were performed by Atlantic Microlab, Inc., Norcross, Ga. Element compositions are within ±0.4% of the calculated values. Fractional moles of water or organic solvents frequently found in some analytical samples of antifolates were not prevented despite 24-48 h of drying in vacuo and were confirmed where possible by their presence in the $^1$H NMR spectra. High resolution mass spectrometry (HRMS) was performed on a Waters Q-TOF (API-US) by Department of Chemistry, University of Pittsburgh, Pittsburgh, Pa. All solvents and chemicals were purchased from Aldrich Chemical Co. and Fisher Scientific and were used as received.

5-(4-Hydroxy-but-1-ynyl)-thiophene-2-carboxylic acid methyl ester (2)

To a 20-mL vial for microwave reaction, were added a mixture of palladium chloride (57 mg, 0.32 mmol), triphenylphosphine (104 mg, 0.32 mmol), copper iodide (243 mg, 1.28 mmol), triethylamine (8.08 g, 80 mmol), 5-bromo-thiophene-2-carboxylic acid methyl ester (1.77 g, 8 mmol) and anhydrous acetonitrile (10 mL). To the stirred mixture, were added copper iodide (243 mg, 1.28 mmol) and but-3-yn-1-ol, 1 (588 mg, 8.4 mmol), and the vial was sealed and put into the microwave reactor at 100° C. for 10 min. After evaporation of solvent under reduced pressure, MeOH (20 mL) was added followed by silica gel (5 g). The resulting plug was loaded on to a silica gel column (3.5×12 cm) and eluted with hexane followed by 20% EtOAc in hexane. Fractions with an R$_f$=0.42 (hexane/EtOAc 4:1) were pooled and evaporated to afford 1.17 g of 2 as yellow oil. $^1$H NMR (DMSO-d$_6$): δ 2.59-2.63 (t, J=6.4 Hz, 2H), 3.56-3.59 (t, J=6.4 Hz, 2H), 3.81 (s, 3H), 4.95-4.98 (t, J=5.6 Hz, 1H), 7.27-7.28 (d, J=4.0 Hz, 1H), 7.69-7.70 (d, J=4.0 Hz, 1H).

5-(4-Hydroxy-butyl)-thiophene-2-carboxylic acid methyl ester (3)

To a Parr flask were added 2 (1.17 g, 5.6 mmol), 10% palladium on activated carbon (600 mg), and MeOH (100 mL). Hydrogenation was carried out at 55 psi of H$_2$ for 4 h. The reaction mixture was filtered through Celite, washed with MeOH (100 mL) and concentrated under reduced pressure to give 1.14 g of 3 as yellow oil. $^1$H NMR (DMSO-d$_6$): δ 1.41-1.48 (m, 2H), 1.61-1.68 (m, 2H), 2.81-

2.85 (t, J=7.2 Hz, 2H), 3.37-3.42 (m, 2H), 3.77 (s, 3H), 4.40-4.43 (t, J=5.2 Hz, 1H), 6.94-6.95 (d, J=3.6 Hz, 1H), 7.63-7.64 (d, J=3.6 Hz, 1H).

5-(3-Carboxy-propyl)-thiophene-2-carboxylic acid methyl ester (4)

A solution of 3 (1.14 g, 5.3 mmol) in acetone (15 mL) was added dropwise to a cold solution (ice bath) of $CrO_3$ (3 g, 30 mmol) in sulfuric acid (23 mL) and water (67 mL). After the addition, the resulting solution was stirred in an ice bath for an additional 2 h and the solution was allowed to warm to room temperature overnight. TLC indicated the disappearance of the starting alcohol and the formation of one major spot at $R_f$=0.35 (hexane/EtOAc 2:1). The solution was extracted with 5×30 mL of ethyl ether and dried over $Na_2SO_4$. After evaporation of the solvent under reduced pressure, the resulting residue was flash chromatographed through silica gel column (3.5×15 cm) using hexane/EtOAc (2:1) as eluent. The desired fraction (TLC) was collected and the solvent was evaporated under reduced pressure to afford 570 mg of 4 as colorless oil. $^1$H NMR (DMSO-$d_6$): δ 1.79-1.87 (m, 2H), 2.24-2.27 (t, J=7.2 Hz, 2H), 2.82-2.86 (t, J=7.2 Hz, 2H), 3.77 (s, 3H), 6.95-6.96 (d, J=3.6 Hz, 1H), 7.63-7.64 (d, J=3.6 Hz, 1H), 12.17 (br, 1H). HRMS calcd for $C_{10}H_{12}O_4S$ (M$^+$), 228.0456; found: 228.0458.

5-(5-Bromo-4-oxo-pentyl)-thiophene-2-carboxylic acid methyl ester (7)

To 4 (570 mg, 2.5 mmol) in a 100 mL flask were added oxalyl chloride (1.9 g, 15 mmol) and anhydrous $CH_2Cl_2$ (20 mL). The resulting solution was refluxed for 1 h and then cooled to room temperature. After evaporating the solvent under reduced pressure, the residue 5 was dissolved in 20 mL of $Et_2O$. The resulting solution was added dropwise to an ice-cooled diazomethane (generated in situ from 10 g of diazald by using Aldrich Mini Diazald Apparatus) in an ice bath over 10 min. The resulting mixture was allowed to stand for 30 min and then stirred for an additional 1 h. To this solution was added 48% HBr (20 mL). The resulting mixture was refluxed for 1.5 h. After cooling to room temperature, the organic layer was separated and the aqueous layer extracted with $Et_2O$ (50 mL×2). The combined organic layer and $Et_2O$ extract was washed with two portions of 10% $Na_2CO_3$ solution and dried over $Na_2SO_4$. Evaporation of the solvent afforded 7 as colorless crystals. $^1$H NMR (CDCl$_3$-d): δ 1.99-2.07 (m, 2H), 2.71-2.75 (t, J=7.2 Hz, 2H), 2.87-2.91 (t, J=7.2 Hz, 2H), 3.87 (s, 3H), 3.88 (s, 2H), 6.81-6.82 (d, J=3.6 Hz, 1H), 7.64-7.65 (d, J=3.6 Hz, 1H). HRMS calcd for $C_{11}H_{13}BrO_3S$ (M$^+$), 303.9769; found: 303.9759.

5-[3-(2-Amino-4-oxo-4,7-dihydro-3H-pyrrolo[2,3-d] pyrimidin-6-yl)-propyl]-thiophene-2-carboxylic acid methyl ester (8)

To a suspension of 2,6-diaminopyrimidin-4-one (315 mg, 2.5 mmol) in anhydrous DMF (15 mL) was added 7 (about 2.4 mmol). The resulting mixture was stirred under $N_2$ at room temperature for 3 days. After evaporation of solvent under reduced pressure, MeOH (20 mL) was added followed by silica gel (1.5 g). The resulting plug was loaded on to a silica gel column (3.5×12 cm) and eluted with CHCl$_3$ followed by 3% MeOH in CHCl$_3$ and then 5% MeOH in CHCl$_3$. Fractions with an $R_f$=0.56 (MeOH/CHCl$_3$ 1:5) were pooled and evaporated to afford 300 mg of 8 as white powder in 38% yield. $^1$H NMR (DMSO-$d_6$): δ 1.89-1.97 (m, 2H), 2.49-2.54 (t, J=7.2 Hz, 2H), 2.82-2.85 (t, J=7.2 Hz, 2H), 3.78 (s, 3H), 5.89 (s, 1H), 5.96 (s, 2H), 6.97-6.98 (d, J=3.6 Hz, 1H), 7.64-7.65 (d, J=3.6 Hz, 1H), 10.13 (s, 1H), 10.82 (s, 1H).

5-[3-(2-Amino-4-oxo-4,7-dihydro-3H-pyrrolo[2,3-d] pyrimidin-6-yl)-propyl]-thiophene-2-carboxylic acid (9)

To a solution of 8 (300 mg, 0.9 mmol) in MeOH (10 mL) was added 1 N NaOH (10 mL) and the mixture was stirred under $N_2$ at room temperature for 16 h. TLC showed the disappearance of the starting material ($R_f$=0.56) and one major spot at the origin (MeOH/CHCl$_3$ 1:5). The reaction mixture was evaporated to dryness under reduced pressure. The residue was dissolved in water (10 mL), the resulting solution was cooled in an ice bath, and the pH was adjusted to 3-4 with dropwise addition of 1 N HCl. The resulting suspension was frozen in a dry ice-acetone bath, thawed to 4-5° C. in the refrigerator, and filtered. The residue was washed with a small amount of cold water and dried in vacuum using $P_2O_5$ to afford 254 mg of 9 as white powder. $^1$H NMR (DMSO-$d_6$): δ 1.89-1.96 (m, 2H), 2.49-2.55 (t, J=7.2 Hz, 2H), 2.80-2.84 (t, J=7.2 Hz, 2H), 5.88 (s, 1H), 5.98 (s, 2H), 6.92-6.93 (d, J=3.6 Hz, 1H), 7.55-7.56 (d, J=3.6 Hz, 1H), 10.14 (s, 1H), 10.83 (s, 1H) 12.86 (br, 1H).

(S)-2-({5-[3-(2-Amino-4-oxo-4,7-dihydro-31H-pyrrolo[2,3-d]pyrimidin-6-yl)-propyl]-thiophene-2-carbonyl}-amino)-pentanedioic acid diethyl ester (10)

To a solution of 9 (254 mg, 0.8 mmol) in anhydrous DMF (10 mL) was added N-methylmorpholine (145 mg, 1.44 mmol) and 2-chloro-4,6-dimethoxy-1,3,5-triazine (253 g, 1.44 mmol). The resulting mixture was stirred at room temperature for 2 h. To this mixture were added N-methylmorpholine (145 mg, 1.44 mmol) and L-glutamate diethyl ester hydrochloride (290 mg, 1.2 mmol). The reaction mixture was stirred for an additional 4 h at room temperature and then evaporated to dryness under reduced pressure. The residue was dissolved in the minimum amount of CHCl$_3$/MeOH (4:1) and chromatographed on a silica gel column (2×15 cm) and with 5% CHCl$_3$ in MeOH as the eluent. Fractions that showed the desired spot (TLC) were pooled and the solvent evaporated to dryness to afford 252 mg of 10 as yellow powder in 63% yield. $^1$H NMR (DMSO-$d_6$): δ 1.14-1.21 (m, 6H), 1.81-2.05 (m, 4H), 2.32-2.39 (t, J=7.6 Hz, 2H), 2.49-2.52 (t, J=7.2 Hz, 2H), 2.78-2.81 (t, J=7.2 Hz, 2H), 4.02-4.07 (m, 4H), 4.30-4.35 (m, 1H), 5.88 (s, 1H), 5.94 (s, 2H), 6.89-6.90 (d, J=3.6 Hz, 1H), 7.68-7.69 (d, J=3.6 Hz, 1H), 8.61-8.63 (d, J=8 Hz, 1H), 10.71 (s, 1H), 11.19 (s, 1H).

(S)-2-({5-[3-(2-Amino-4-oxo-4,7-dihydro-3H-pyrrolo[2,3-d]pyrimidin-6-yl)-propyl]-thiophene-2-carbonyl}-amino)-pentanedioic acid (AAG154544)

To a solution of 10 (252 mg, 0.5 mmol) in MeOH (10 mL) was added 1 N NaOH (10 mL) and the mixture was stirred under $N_2$ at room temperature for 16 h. TLC showed the disappearance of the starting material ($R_f$=0.48) and one major spot at the origin (MeOH/CHCl$_3$ 1:5). The reaction mixture was evaporated to dryness under reduced pressure. The residue was dissolved in water (10 mL), the resulting solution was cooled in an ice bath, and the pH was adjusted to 3-4 with dropwise addition of 1 N HCl. The resulting suspension was frozen in a dry ice-acetone bath, thawed to 4-5° C. in the refrigerator, and filtered. The residue was washed with a small amount of cold water and dried in vacuum using $P_2O_5$ to afford 212 mg (95%) of AAG154544 as white powder. mp 175-176° C.; $^1$H NMR (DMSO-$d_6$): δ 1.88-2.10 (m, 4H), 2.31-2.34 (t, J=7.6 Hz, 2H), 2.49-2.54 (t, J=7.2 Hz, 2H), 2.78-2.81 (t, J=7.2 Hz, 2H), 4.30-4.35 (m, 1H), 5.88 (s, 1H), 5.97 (s, 2H), 6.89-6.90 (d, J=3.6 Hz, 1H), 7.68-7.69 (d, J=3.6 Hz, 1H), 8.50-8.52 (d, J=8 Hz, 1H), 10.13 (s, 1H), 10.82 (s, 1H) 12.42 (br, 2H). Anal. ($C_{19}H_{21}N_5O_6S$) C, H, N, S. calcd for $C_{19}H_{21}N_5O_6S.1H_2O$: C, 49.02; H, 4.98; N, 15.05; S, 6.89. Found: C, 49.22; H, 4.80; N, 15.03; S, 6.97.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims

The invention claimed is:

1. A compound of Formula I:

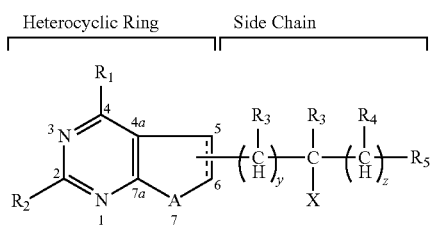

I wherein $R_1$ is one of (a) a hydrogen (H)), (b) an OH, (c) a $CH_3$, and (d) NHR wherein R is either a H or an alkyl group having from 1 to 6 carbon atoms, and tautomers of said (b) and said (d);

$R_2$ is one of (a) a hydrogen (H), (b) a $CH_3$, (c) an OH, and (d) NHR wherein R is either a H or an alkyl group having from 1 to 6 carbon atoms;

A is an oxygen (O);

wherein the bond at position 5-6 may either be a single or a double bond;

wherein the five membered ring has a side chain attached at positions 5 or 6, and optionally includes wherein the carbon atoms at positions 5 and 6, independently, have attached thereto either (a) two hydrogen atoms if the bond between carbon atoms 5 and 6 is a single bond or one hydrogen atom if the bond between carbon atoms 5 and 6 is a double bond, or (b) an alkyl group having from one to six carbon atoms and a hydrogen atom if the bond between carbon atoms at positions 5 and 6 is a single bond or an alkyl group having from one to six carbon atoms if the bond between carbon atoms 5 and 6 is a double bond, and combinations thereof, and $R_3$ is one of (a) a hydrogen (H), (b) $CH_3$, (c) trifluoromethyl, (d) difluoromethyl, (e) monofluoromethyl, (f) methyl ketone, (g) trifluoromethyl ketone, (h) difluoromethyl ketone, (i) monofluoromethyl ketone, (j) formyl, (k) methyl alcohol, (l) methylamine, or (m) a bond;

X is either a heterocycloalkyl-carbonyl-L-glutamate group, a heterocycloaryl-carbonyl-L-glutamate group, or a hydrogen (H), and wherein X is a hydrogen then $R_4$ is a heterocycloalkyl-carbonyl-L-glutamate group or a heterocycloaryl-carbonyl-L-glutamate group, and wherein X is heterocycloalkyl-carbonyl-L-glutamate group or a heterocycloaryl-carbonyl-L-glutamate group then $R_4$ is a hydrogen or a bond;

wherein $R_5$ is the same as $R_3$ except that $R_5$ is not a bond;

y is an integer ranging from zero up to and including 6;

z is an integer ranging from zero up to and including seven, and the sum total of integers y and z is equal to zero, 5, 6, or 7.

2. The compound of claim 1 comprising wherein said heterocycloalkyl-carbonyl-L-glutamate group is selected from the group consisting of a dihydrothiophene-carbonyl-L-glutamate group, a tetrahydrothiophene-carbonyl-L-glutamate group, a dihydrofuran-carbonyl-L-glutamate group, a tetrahydrofuran-carbonyl-L-glutamate group, a dihydropyrrole-carbonyl-L-glutamate group, a tetrahydropyrrole-carbonyl-L-glutamate group, a monohydropyridyl-carbonyl-L-glutamate group, a dihydropyridyl-carbonyl-L-glutamate group, and a piperidyl-carbonyl-L-glutamate group, and stereoisomers thereof.

3. The compound of claim 1 wherein said heterocycloaryl-carbonyl-L-glutamate group is selected from the group consisting of a thiophene-carbonyl-L-glutamate group, a furan-carbonyl-L-glutamate group, a pyrrole-carbonyl-L-glutamate group, and a pyridine-carbonyl-L-glutamate group.

4. A pharmaceutically acceptable salt of the compound of Formula I:

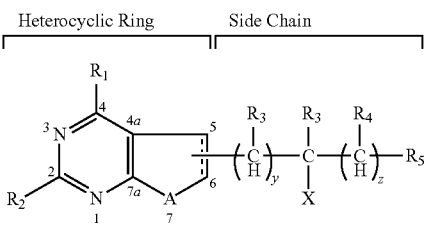

I wherein $R_1$ is one of (a) a hydrogen (H)), (b) an OH, (c) a $CH_3$, and (d) NHR wherein R is either a H or an alkyl group having from 1 to 6 carbon atoms, and tautomers of said (b) and said (d);

$R_2$ is one of (a) a hydrogen (H), (b) a $CH_3$, (c) an OH, and (d) NHR wherein R is either a H or an alkyl group having from 1 to 6 carbon atoms;

A is an oxygen (O);

wherein the bond at position 5-6 may either be a single or a double bond;

wherein the five membered ring has a side chain attached at positions 5 or 6, and optionally includes wherein the carbon atoms at positions 5 and 6, independently, have attached thereto either (a) two hydrogen atoms if the bond between carbon atoms 5 and 6 is a single bond or one hydrogen atom if the bond between carbon atoms 5 and 6 is a double bond, or (b) an alkyl group having from one to six carbon atoms and a hydrogen atom if the bond between carbon atoms at positions 5 and 6 is a single bond or an alkyl group having from one to six carbon atoms if the bond between carbon atoms 5 and 6 is a double bond, and combinations thereof, and $R_3$ is one of (a) a hydrogen (H), (b) $CH_3$, (c) trifluoromethyl, (d) difluoromethyl, (e) monofluoromethyl, (f) methyl ketone, (g) trifluoromethyl ketone, (h) difluoromethyl ketone, (i) monofluoromethyl ketone, (j) formyl, (k) methyl alcohol, (l) methylamine, or (m) a bond;

X is either a heterocycloalkyl-carbonyl-L-glutamate group, a heterocycloaryl-carbonyl-L-glutamate group, or a hydrogen (H), and wherein X is a hydrogen then $R_4$ is a heterocycloalkyl-carbonyl-L-glutamate group or a heterocycloaryl-carbonyl-L-glutamate group, and wherein X is a a heterocycloalkyl-carbonyl-L-glutamate group or a heterocycloaryl-carbonyl-L-glutamate group then $R_4$ is a hydrogen or a bond;

wherein $R_5$ is the same as $R_3$ except that $R_5$ is not a bond;

y is an integer ranging from zero up to and including 6;

z is an integer ranging from zero up to and including seven, and the sum total of integers y and z is equal to zero, 5, 6, or 7.

5. A pharmaceutical composition of a therapeutically effective amount of a compound of Formula I, or a pharmaceutically acceptable salt of Formula I:

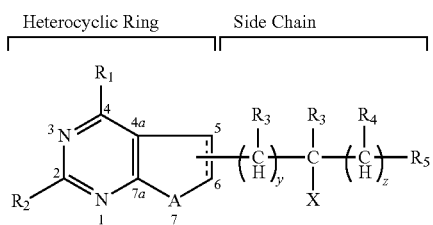

I wherein $R_1$ is one of (a) a hydrogen (H)), (b) an OH, (c) a $CH_3$, and (d) NHR wherein R is either a H or an alkyl group having from 1 to 6 carbon atoms, and tautomers of said (b) and said (d);

$R_2$ is one of (a) a hydrogen (H), (b) a $CH_3$, (c) an OH, and (d) NHR wherein R is either a H or an alkyl group having from 1 to 6 carbon atoms;

A is an oxygen (O);

wherein the bond at position 5-6 may either be a single or a double bond;

wherein the five membered ring has a side chain attached at positions 5 or 6, and optionally includes wherein the carbon atoms at positions 5 and 6, independently, have attached thereto either (a) two hydrogen atoms if the bond between carbon atoms 5 and 6 is a single bond or one hydrogen atom if the bond between carbon atoms 5 and 6 is a double bond, or (b) an alkyl group having from one to six carbon atoms and a hydrogen atom if the bond between carbon atoms at positions 5 and 6 is a single bond or an alkyl group having from one to six carbon atoms if the bond between carbon atoms 5 and 6 is a double bond, and combinations thereof;

$R_3$ is one of (a) a hydrogen (H), (b) $CH_3$, (c) trifluoromethyl, (d) difluoromethyl, (e) monofluoromethyl, (f) methyl ketone, (g) trifluoromethyl ketone, (h) difluoromethyl ketone, (i) monofluoromethyl ketone, (j) formyl, (k) methyl alcohol, (l) methylamine, or (m) a bond;

X is either a heterocycloalkyl-carbonyl-L-glutamate group, a heterocycloaryl-carbonyl-L-glutamate group, or a hydrogen (H), and wherein X is a hydrogen then $R_4$ is a heterocycloalkyl-carbonyl-L-glutamate group or a heterocycloaryl-carbonyl-L-glutamate group, and wherein X is a heterocycloalkyl-carbonyl-L-glutamate group or a heterocycloaryl-carbonyl-L-glutamate group then $R_4$ is a hydrogen or a bond;

wherein $R_5$ is the same as $R_3$ except that $R_5$ is not a bond;

y is an integer ranging from zero up to and including 6;

z is an integer ranging from zero up to and including seven, and the sum total of integers y and z is equal to zero, 5, 6, or 7.

6. The pharmaceutical composition of claim 5 wherein said heterocycloalkyl-carbonyl-L-glutamate group is selected from the group consisting of a dihydrothiophene-carbonyl-L-glutamate group, a tetrahydrothiophene-carbonyl-L-glutamate group, a dihydrofuran-carbonyl-L-glutamate group, a tetrahydrofuran-carbonyl-L-glutamate group, a dihydropyrrole-carbonyl-L-glutamate group, a tetrahydropyrrole-carbonyl-L-glutamate group, a monohydropyridyl-carbonyl-L-glutamate group, a dihydropyridyl-carbonyl-L-glutamate group, and a piperidyl-carbonyl-L-glutamate group, and stereoisomers thereof.

7. The pharmaceutical composition of claim 5 wherein said heterocycloaryl-carbonyl-L-glutamate group is selected from the group consisting of a thiophene-carbonyl-L-glutamate group, a furan-carbonyl-L-glutamate group, a pyrrole-carbonyl-L-glutamate group, and a pyridine-carbonyl-L-glutamate group.

* * * * *